US 9,370,562 B2

(12) United States Patent
Nikolin et al.

(10) Patent No.: US 9,370,562 B2
(45) Date of Patent: Jun. 21, 2016

(54) SCHMALLENBERG VIRUS (SBV) VACCINE, METHODS OF PRODUCTION, AND USES THEREOF

(71) Applicants: Veljko Nikolin, Hannover (DE); Konrad Stadler, Celle (DE); Axel Lischewski, Ockenheim (DE); Alexander Brix, Saint Joseph, MO (US); Jeffrey P. Knittel, Parkville, MO (US); Katharina Hedwig Toepfer, Hannover (DE)

(72) Inventors: Veljko Nikolin, Hannover (DE); Konrad Stadler, Celle (DE); Axel Lischewski, Ockenheim (DE); Alexander Brix, Saint Joseph, MO (US); Jeffrey P. Knittel, Parkville, MO (US); Katharina Hedwig Toepfer, Hannover (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 9 days.

(21) Appl. No.: 13/904,752

(22) Filed: May 29, 2013

(65) Prior Publication Data
US 2013/0323277 A1 Dec. 5, 2013

(30) Foreign Application Priority Data

Jun. 1, 2012 (EP) .................... 12170631
Mar. 5, 2013 (EP) .................... 13157875

(51) Int. Cl.
*A61K 39/12* (2006.01)
*A61K 35/76* (2015.01)
*A61K 39/00* (2006.01)

(52) U.S. Cl.
CPC ............... *A61K 39/12* (2013.01); *A61K 35/76* (2013.01); *A61K 2039/5252* (2013.01); *A61K 2039/552* (2013.01); *A61K 2039/55505* (2013.01); *A61K 2039/55577* (2013.01); *C12N 2760/12022* (2013.01); *C12N 2760/12034* (2013.01); *C12N 2760/12063* (2013.01)

(58) Field of Classification Search
None
See application file for complete search history.

(56) References Cited

U.S. PATENT DOCUMENTS

2008/0226682 A1* 9/2008 Brake et al. ................. 424/278.1
2013/0323210 A1 12/2013 Reimann et al.
2013/0323277 A1 12/2013 Nikolin et al.

OTHER PUBLICATIONS

Bridgen and Elliott, Rescue of a segmented negative-strand RNA virus entirely from cloned complementary DNAs, 1996, PNAS, vol. 93., pp. 15400-15404.*
GenBank Accession # HE649912, Schmallenberg virus RdRp gene for RNA-dependent RNA polymerase, segment L, genomic RNA, isolate BH80/11-4, published Mar. 26, 2012.*
GenBank Accession # HE649914, Schmallenberg virus genes for nucleocapsid protein and non-structural protein, segment S, genomic RNA, isolate BH80/11-4, published Mar. 26, 2012.*
GenBank Accession # HE649913, Schmallenberg virus gene for M polyprotein, segment M, genomic RNA, isolate BH80/11-4, published Mar. 26, 2012.*
Lytle and Sagripanti, Predicted Inactivation of Viruses of Relevance to Biodefense by Solar Radiation, 2005, Journal of Virology, vol. 79, No. 22, pp. 14244-14252.*
Doceul et al., Epidemiology, molecular virology and diagnostics of Schmallenberg virus, an emerging orthobunyavirus in Europe, 2013, Veterinary Research, vol. 44, No. 31, pp. 1-13.*
EMBL Accession No. HE649914, Hoeper, D., "Schmallenberg virus genes for nucleocapsid protein and non-structural protein, segment S, genomic RNA, isolate BH80/11-4"., Frederick-Loeffler-Institute, Jan. 16, 2012, 2 pages.
Elliott et al., "Establishment of a reverse genetics system for Schmallenberg virus, a newly emerged orthobunyavirus in Europe". Journal of General Virology, vol. 94, No. 4, Apr. 2013, pp. 851-859.
Garigliany et al., "Schmallenberg virus: A new Shamonda/Sathuperi-like virus on the rise in Europe". Antiviral Research, vol. 95, No. 2, May 2012, pp. 82-87.
Hoffmann et al., "Novel Orthobunyavirus in Cattle, Europe, 2011". Emerging Infectious Diseases, vol. 18, No. 3, Mar. 2012, pp. 469-472.
Ikegami et al., "Rift Valley fever vaccines". Vaccine, vol. 27, Nov. 2009, pp. D69-D72.
International Search Report and Written Opinion for PCT/US2013/043146 mailed Jul. 18, 2013.
Wernike et al., "Inactivated Schmallenberg virus prototype vaccines". Vaccine, vol. 31, May 2013, pp. 3558-3563.
Wernike et al., "Schmallenberg virus challenge modesl in cattle: infectious serum or culture-grown virus". Veterinary Research, vol. 43, No. 1, Dec. 2012, pp. 84-87.
Yanase et al., "Genetic reassortment between Sathuperi and Shamonda viruses of the genus Orthobunyavirus in nature: implications for their genetic relationship to Schmallenberg virus". Archives of Virology, vol. 157, No. 8, May 2012, pp. 1611-1616.
Beer et al., "Update—Information from the Friedrich-Loeffler-Institut on 'Schmallenberg Virus': Accessions No. of full-length sequences available". Friedrich-Loeffler-Institut, Jan 16, 2012, 1 page. [Accessed at http://www.fli.bund.de/fileadmin/dam_uploads/tierseuchen/Schmallenberg_Virus/Schmallenberg-Update_20120116-en.pdf on Jul. 9, 2013].
EMBL Accession No. HE649913, Hoffman et al., "Schmallenberg virus gene for M polyprotein, segment M, genomic RNA, isolate BH80/11-4"., Frederick-Loeffler-Institute, Jan. 16, 2012, 3 pages.

(Continued)

*Primary Examiner* — Benjamin P Blumel
(74) *Attorney, Agent, or Firm* — Michael P. Morris; Wendy M. Gombert

(57) ABSTRACT

The present invention relates to the field of vaccines and medicaments for the prophylaxis and treatment of infectious diseases in ruminants. In particular, it relates to inactivated Schmallenberg virus (SBV) useful as vaccine or medicament for preventing or treating viremia, the transmission and clinical symptoms, in particular malformations in newborn ruminants such as cattle, sheep and goats, induced by SBV.

19 Claims, No Drawings

(56) References Cited

OTHER PUBLICATIONS

EMBL Accession No. HE6499132, Hoffman et al., "Schmallenberg virus RdRp gene for RNA-dependent RNA polymerase, segment L, genomic RNA, isolate BH80/11-4"., Frederick-Loeffler-Institute, Jan. 16, 2012, 4 pages.

Varela et al., "Schmallenberg Virus Pathogenesis, Tropism and Interaction with the Innate Immune System of the Host". PLOS Pathogens, vol. 9, No. 1, e1003133, Jan. 2013, pp. 1-13.

Mettenleiter et al., "Information from the Friedrich-Loeffler-Institut on 'Schmallenberg Virus'". Friedrich-Loeffler-Institut, Jan. 10, 2012, 1 page. [Accessed at http://www.fli.bund.de/fileadmin/dam_uploads/tierseuchen/Schmallenberg_Virus/FLIInformation_Schmallenberg-20120110.pdf on Jul. 9, 2013].

Bennett et al., "A Recombinant Chimeric La Crosse Virus Expressing the Surface Glycoproteins of Jamestown Canyon Virus Is Immunogenic and Protective against Challenge with either Parental Virus in Miche or Monkeys". Journal of Virology, vol. 86, No. 1, 2012, pp. 420-426.

* cited by examiner

SEQUENCE LISTING

```
<160> NUMBER OF SEQ ID NOS: 8

<210> SEQ ID NO 1
<211> LENGTH: 839
<212> TYPE: DNA
<213> ORGANISM: Schmallenberg virus

<400> SEQUENCE: 1
agtagtgagc tccactatta actacagaaa tatgtcaagc caattcattt ttgaagatgt    60
accacaacgg aatgcagcta catttaaccc ggaggtcggg tatgtggcat ttattggtaa   120
gtatgggcaa caactcaact tcggtgttgc tagagtcttc ttcctcaacc agaagaaggc   180
caagatggtc ctacataaga cggcacaacc aagtgtcgat cttacttttg gtggggtcaa   240
atttacagtg gttaataacc attttcccca atatgtctca aatcctgtgc cagacaatgc   300
cattacactt cacaggatgt caggatatct agcacgttgg attgctgata catgcaaggc   360
tagtgtcctc aaactagctg aagctagtgc tcagattgtc atgccccttg ctgaggttaa   420
gggatgcacc tgggccgatg gttatacaat gtatcttgga tttgcacctg gggccgaaat   480
gttccttgat gcttttgact tctatccact agttattgaa atgcataggg tcctcaagga   540
caatatggat gtaaatttta tgaaaaaagt cctccgccaa cgctatggaa caatgactgc   600
tgaagaatgg atgactcaga aaataacaga aataaaagct gcttttaatt ctgttggaca   660
gcttgcctgg gccaaatctg gattctctcc tgctgctaga accttcttgc agcaattcgg   720
tatcaacatc taaacctctt catcacagat cttcaatttc cgtgcaatat gtctatgtat   780
```
tgcacaccat tatactgcaa ggcttctgtt aagatagtta ataagtggag aacactact    839

<210> SEQ ID NO 2
<211> LENGTH: 4373
<212> TYPE: DNA
<213> ORGANISM: Schmallenberg virus

<400> SEQUENCE: 2
agtagtgaac taccacaatc aaaatgcttc tcaacattgt cttgatatct aacttagcct      60
gtttagcttt tgcactccca cttaaggaag gcactagagg gtctaggtgc ttcctgaatg     120
gcgaactggt taaaactgtt aacacatcaa aggtcgtttc agaatgctgt gtgaaagacg     180
acatatctat cattaaatca aatgctgaac attataaatc aggagatcgg ttggctgctg     240
taataaaata ttatcgttta tatcaggtga aggattggca ttcttgcaat ccaatttatg     300
atgaccacgg ttcctttatg atattagata tagataatac tggcacatta atccctaaaa     360
tgcatacatg cagagttgaa tgcgaaatag cactgaataa agatactggc gaagttatat     420
tgaattcata tcgaattaac cactaccgaa tctcgggcac aatgcatgta tcaggttggt     480
ttaaaaacaa aattgagatt cctttggaaa acacatgcga atccattgag gtaacatgtg     540
gattaaaaac acttaatttt catgcatgtt tccatcccca taagtcatgc accgctatt      600
ttaaaggatc aatcctgccg gaattgatga tcgaatcatt tgtacgaatt cttgaattaa     660
tactgctagt aactttcata ttagtttggg ctgtcatgat gatgatattg acgaaaacat     720
atatagtata tgtgttcatt cctatatttt atccatttgt gaaattatat gcttatatgt     780
acaacaaata ttttaaattg tgtaaaaatt gcctgttagc agtacatccc tttacaaatt     840
gcccatcgac atgcatctgt ggaatgattt acactaccac tgaatcactc aaattgcatc     900
gcatgtgtaa caattgttct ggctataaag cattgccgaa acaaggaaa ttgtgtaaaa       960
gtaaaatatc aatatagtg ctatgtgtga taacatcact gatatttttc tcatttatca     1020
cacctatatc gagtcaatgt atcgatatag aaaaactgcc agacgagtat attacatgta     1080
aaagagagct agctaatatc aaaagcttga caattgatga cacatatagc tttatatatt     1140
cctgtacatg cataattgtg ttaatattac ttaaaaggc agcaaagtat atcttgtact     1200
gcaactgcag cttttgtggt atggtacatg aacgacgtgg attgaagata atggacaact     1260
ttacaaacaa gtgcctaagt tgtgtatgcg cagaaaacaa gggcttaaca attcacagag     1320
cctctgagaa atgtctgttc aaatttgaat caagttataa taggaccggg ttgataatct     1380
ttatgcttct gttagtccca acaattgtaa tgacgcaaga actagtatt aactgcaaaa      1440
acattcaatc aactcagctt acaatagagc acctgagtaa gtgcatggca ttttatcaaa     1500
ataaaacaag ctcaccagtt gtaatcaatg aaataatttc agatgcttca gtagacgaac     1560
aagaattaat aaaaagttta aacttgaact gtaatgtcat agataggttt atttccgaat     1620
ctagtgttat tgagactcaa gtttattatg agtatataaa atcacagttg tgccctctcc     1680
aagtgcatga tattttcact atcaattcag caagtaacat acaatggaaa gcactggccc     1740
gaagtttcac cttaggagtg tgcaatacga atcctcataa acatatatgt agatgcttgg     1800
agtctatgca aatgtgcaca tcaaccaaga cagaccacgc tagggaaatg tcaatatatt     1860
atgatggtca tccagatcgc tttgagcatg acatgaaaat aatattgaat ataatgagat     1920
atatagtccc tggattaggt cgagtcttgc ttgatcaaat caaacaaaca aaagactacc     1980
aagctttacg ccacatacaa ggtaagcttt ctccctaaatc gcagtcaaat ttacaactta     2040
aaggatttct ggaatttgtt gattttatcc ttggtgcaaa cgtgacaata gaaaaaaccc     2100

```
ctcaaacatt aactacatta tctttgataa aaggagccca cagaaacttg gatcaaaaag    2160
atccaggtcc aacaccaata ctggtatgca aatcaccaca aaaagtggta tgctactcac    2220
cacgtggtgt cacacaccca ggagattata tatcatgcaa atctaagatg tataagtggc    2280
catctttagg ggtatacaaa cataatagag accagcaaca agcctgcagc agtgacacac    2340
attgcctaga gatgtttgaa ccagcagaaa gaacaataac tacaaaaata tgcaaagtaa    2400
gtgatatgac ttattcagaa tcgccatata gtactggaat accatcatgc aacgtgaaga    2460
gatttggatc atgtaatgta aggggtcatc aatggcaaat tgcagaatgc tcaaatggct    2520 tatttttacta tgtttcagct aaagcccatt cgaaaactaa cgatataaca ctgtactgtt    2580
tatcagcaaa ttgcctggac ttgcgttatg cattcagatc cagtagttgt tcagatatag    2640
tatgggatac aagttatcga aataaattaa caccaataatc tattaatcat ccagatattg    2700
aaaactacat agcagcgctt cagtcagata ttgcaaatga tttaactatg cactactta    2760 aaccattaaa aaaccttcca gcaataattc ctcaatacaa aacaatgaca ttgaatgggg    2820
acaaggtatc aaatggtatt agaaatagtt atatcgagtc gcacatccct gcaattaatg    2880
gtttatcagc agggattaat attgccatgc caaatggaga aagcctcttt tccattatta    2940
tctatgtcag aagagtaata aataaagcat cgtatcgatt tctatatgaa acaggaccca    3000
caattggaat aaatgccaag cacgaagagg tatgtaccgg gaagtgccca agcccaatac    3060
cacatcaaga tggttgggtc acattctcaa aggaaagatc aagtaattgg ggctgtgaag    3120 aatgggttg cttggcaata aatgatggtt gtttatatgg gtcatgtcaa gacataataa    3180
ggcctgaata taagatatac aagaagtcta gtattgaaca aaaggatgtt gaagtttgta    3240
taaccatggc ccatgaatca ttctgcagta ccgttgatgt tctccaacct ttaattagcg    3300
acaggataca attagatatc caaacgattc aaatggactc tatgccaaat ataattgcag    3360
tcaagaatgg gaaagtttat gttggagata tcaatgactt aggttcgaca gcaagaaat    3420 gtggctcagt ccaattatat tctgaaggga tcattggatc gggaaccccca aaatttgatt    3480 atgtttgcca tgcattcaat cgtaaagatg tcatccttcg aagatgcttt gataactcat    3540
atcagtcttg tcttctcttg gaacaagata atacattaac tattgcttct accagtcata    3600
tggaagtgca taaaaaagtt tcaagcgtgg gtacaatcaa ttataaaatt atgttagggg    3660
attttgacta caatgcatat tcaacacaag caacagtcac aatagatgag atcaggtgtg    3720
gtggttgtta tggctgccct gaaggaatgg cttgcgcact caaattgagt accaatacca    3780
tcgggagttg ttcaataaaa agtaactgcg atacatacat taaaataata gcagtcgatc    3840
cgatgcagag cgagtattcc attaagttaa actgcccact agcaacagag acagtttcag    3900
taagtgtgtg ctcagcttct gcttacacaa aaccttcaat atctaaaaat caaccaaaaa    3960
ttgttttgaa ttccttagat gaaacatctt acatcgagca acatgataaa aagtgttcta    4020
catggctttg cagagtttat aaagaaggga ttagcgtaat atttcagcct ctatttggca    4080
acctatcttt ctattggaga ctgacaatat atataataat ctctttgatt atgctaattc    4140
tgtttctata catattaata ccactgtgca aacggctaaa aggtttattg gaatacaatg    4200
agagaatata ccaaatggaa aataaattta agtgataagc cttataacaa tgagcaatta    4260
taaatgaata aataaaaaca ataaagata aacaaataac aacatatata tgtggttaca    4320
catatatatg taattattca gctgagaagt ttttcatgtg gtagaacact act    4373

<210> SEQ ID NO 3
```

<211> LENGTH: 6882
<212> TYPE: DNA
<213> ORGANISM: Schmallenberg virus

<400> SEQUENCE: 3

| | | | | | |
|---|---|---|---|---|---|
| agtagtgtac | ccctaattac | aatcactatg | gagacataca | agattaacat | ttttagagat | 60 |
| aggatcaacc | agtgtcgaag | tgctgaagaa | gccaaagaca | ttgttgctga | tcttctcatg | 120 |
| gctagacatg | actactttgg | tagagaggta | tgttattacc | tggatatcga | attccggcag | 180 |
| gatgttccag | cttacgacat | acttcttgaa | tttctgccag | ctggcactgc | tttcaacatt | 240 |
| cgcaattgta | caccagacaa | ttttatcatt | cacaatggca | agctttatat | cattgactat | 300 |
| aaagtatcaa | ctgatcatgc | atatggtcaa | aaaacttatg | aaaagtacac | ccagatcttt | 360 |
| ggagacgcat | tgtcagaatt | gccgtttgat | tttgaagttg | tgatcatccg | tgctgaccct | 420 |
| ctgcgagata | ctatccatgt | taattcaaat | caattcttgg | aaatatttgg | gccgctcaac | 480 |
| ataaaccttg | attttacttg | gttctttaat | ttgcgatccc | tgatatatga | gaaatataag | 540 |
| gatgacgaca | gattcctaga | aattgtgaat | caaggtgaat | ttacgatgac | tggaccctgg | 600 |
| attgatgagg | ataccccgga | gctctattca | caccctgtct | ttttggaatt | ctatgattct | 660 |
| ttagatgaga | tggctaaact | gacattccat | gagtctatga | catttgatgc | aactcgcggt | 720 |
| gagaaatgga | atcaaaatct | acaaaaggtt | ataaatagat | atggcaatga | ttataacatt | 780 |
| tttgtgaaag | aggccgctgc | aggaatcttt | agatgtgaag | ggaactaccc | aaaaccaaat | 840 |
| catgatgaaa | tcacaatcgg | ttggaatcaa | atggttcaaa | gagtgagtac | tgagagaaac | 900 |
| ctgactcaag | atgtcagcaa | gcaaaaacca | tctattcatt | tcatatgggg | tcaacctgac | 960 |
| gaaacatcaa | atgcgacaac | accaaaacta | atcaagattg | caaaagcact | ccaaaatatt | 1020 |
| tctggcgagt | ctacatatat | aagcgcattc | agagcattgg | gtatgcttat | ggactttcct | 1080 |
| gagaacacag | ctttatatga | agcacacact | agcaaactaa | aaagtatggc | aagacagaca | 1140 |
| tcgaaaagaa | ttgatactaa | actggaacca | atcaaaatag | gcacggcgac | aatttattgg | 1200 |
| gaacagcagt | ttaaactgga | tactgaaata | atgaatacaa | agacaaatc | acatttgcta | 1260 |
| aaagattttc | ttggcatagg | gggtcacgtg | caattttcaa | aaaagaccat | tgacgatttg | 1320 |
| gatactgaca | aacctactat | attagatttc | aacaaaaagg | aagtcattga | tttttgcaaa | 1380 |
| ttccagtatg | aaaatgtaaa | gaaaatacta | tccggagata | taatctaga | gcgtatagga | 1440 |
| tgttatttag | aagaatatgg | tgcaaatatt | gcatcatgtt | caaggatac | atgggatcag | 1500 |
| attaaccaga | tagggaagtc | aaattactgg | gcttgtatta | aagatttttc | agtcttgatg | 1560 |
| aaaaatatgt | tggcagtttc | tcaatataat | aggcacaata | cttttcgtgt | agtgtgttgt | 1620 |
| gcaaacaata | atctgtttgg | gtttgtaatg | ccttcttctg | atattaaagc | aaagcgatcc | 1680 |
| acacttgttt | acttcttagc | tgtgttgcat | tctactcctc | agaatgtgat | gcaccacggt | 1740 |
| gcattgcatg | cgacatttaa | aactggttca | aaataccttta | gtatctctaa | aggaatgcgt | 1800 |
| ttagataaag | aacgatgtca | acgcatagtt | agttcaccgg | gacttttttat | gttgactaca | 1860 |
| ttgatgtttg | caggagacaa | tccgacactc | aatttgactg | atgtcatgaa | ttttacattc | 1920 |
| cacacttccc | tgtctataac | caaagctatg | ctgtcattga | cagaaccatc | aagatatatg | 1980 |
| ataatgaatt | cattagccat | atccagtcat | gttagagatt | atatagcaga | aaatttggc | 2040 |
| ccttatacaa | agaccagctt | ctctgtagta | atggcaaact | tgattaaaag | gggatgttat | 2100 |
| atggcatata | atcaaagaga | taagtagac | atgaggaata | tctgcctaac | agattatgaa | 2160 |
| ataactcaaa | aaggtgtgag | agataacaga | gacctatcat | caatctggtt | tgaaggctat | 2220 |

```
gtatcactaa aagaatatat taaccaaata tatctaccat tttacttcaa ttcaaaaggt    2280
ttgcatgaaa agcatcatgt tatgatagat ctggctaaga caatcttaga tatagaaagg    2340
gaccagagat taaatatccc aggaatatgg tctacaacac ctagaaaaca aactgcaaat    2400
ttaaatataa ctatctatgc agttgcaaaa aatctaataa tggacactgc tagacataat    2460
tatattagat cacggataga aaacacaaac aacttaaata gatcgatatg cactatttct    2520 acattccacca gctctaaatc atgtattaaa gtaggcgact tgagaaaga aaaagctca     2580 gcaacaaaaa aggctgcaga ttgcatgtca aaagagataa agaagtatac aattgcaaac    2640
ccagaatttg ttgatgaaga gttactaaat gcaactataa gacattcacg ctatgaagac    2700
ttaaaaaaag caatcccgaa ttatattgac attatgtcaa ctaaagtatt tgattctctg    2760
taccagaaaa taaaaggaa ggagatagat gataaaccca ctgtgtatca tatactctct      2820
gctatgaaga atcacacaga ttttaagttt acattcttta acaaaggcca aaaaacagca    2880
aaggataggg aaatattcgt aggcgaattt gaggcaaaaa tgtgcttgta tttagtggag    2940
aggatatcta agaacgctg taagttgaat ccagatgaga tgattagtga accaggcgat      3000
tctaaattga aaaattaga agagcttgca gagtctgaaa tacgattcac agcagcaact    3060
atgaaacaga tcaaagaacg ctatttagca gaaatgggag aagcaagcca tatgatcgca    3120
tataaaccac attctgttaa gattgaaatc aatgcagaca tgtcaaaatg gagtgcccaa    3180
gatgttttat tcaaatattt ctggttgttt gcattagatc ccgcactta tctgcaagaa     3240 aaagaaagga tattgtactt cctatgcaat tatatgcaaa aaaagctaat tctgcctgat    3300
gaaatgctct gtagcatcct tgaccaacgt atcaaacatg aggatgatat aatatatgaa    3360
atgaccaatg gcttatcgca aaattgggtc aatattaaac ggaactggct gcaggggaat    3420
ctcaattaca caagtagcta cctacattca tgttctatga atgtttataa ggatattcta    3480
aagagagcag ccacttact agaagggga gttttagtca attctatggt tcattctgat      3540
gacaatcaca cttcaatagt gatgatccaa gataaattag atgatgatat tgttattgaa    3600
ttttctgcaa aactatttga aaaaatatgt ctaacttttg gaaatcaagc aaatatgaag    3660
aagacatata taacaaattt cataaaggag ttcgtttcac tttttaatat ttatggtgag    3720
ccattttctg tttatggtcg ctttattttg acatctgttg gcgattgtgc ttttcttgga    3780
ccatatgagg atgttgccag taggttgtct gcaacgcaga cagcaattaa gcatggagca    3840
cctccatcac ttgcatggac tgctattgca ttaactcagt ggataacaca tagcacatat    3900
aacatgcttc caggtcaaat caatgatcct acttcatctt tacctagtca tgatagattt    3960
gagctgccta tagaattgtg tggcttaata aattcagaat tacccactat agctatagca    4020
ggtttggaag cagataatct aagttattta gttaggttat caaaaagaat gtcccctata    4080
catctttgcc gtgaaccaat ccagcatcaa tatgagaata tacatacatg gatataagt     4140 aaactgacac aatgtgatat tttcagactt aagcttttaa gatacatgac gttagactca    4200
actatgtcat ctgatgatgg aatgggcgaa actagtgaaa tgagatctag gtctcttctg    4260
acaccaagaa aattcactac tgcaagttcg ttatctagat tgcattcata tgctgattat    4320
caaaaaacaa tacaagacca acagaaaatt gaagaattat ttgaatattt tatagccaac    4380
cctcaactat tggttacaaa aggtgagact tgtgaagagt tctgtatgtc tgtattgttc    4440
agatacaaca gtcgtaaatt taagaatca ttgtctattc aaaacccagc tcagctcttc      4500
atagaacaag tattgtttgc aaataaacca atgatagact atacaagtat tcatgatagg    4560
```

-continued

```
ttgtttggta tacaagatga cccaaatata aatgatgcta catgtattat tggcaagaag    4620
acttttgttg aaacatatca gcaaataaaa attgatgtag aaaaatttac acttgatgta    4680
gaggatataa agacgatata tagcttctgt ataatgaacg accctatatt agttgcttgt    4740
gcaaacaact tgttaatttc aatacaggga gtggagatgc aacgattggg tatgacatgc    4800
tgttatatgc cggagattaa gagccttaaa gtaatttatc atagtcctgc tctcgtatta    4860
cgtgcttatg taacagataa ctatgagcaa aaagggatgg agccagatga aatgcggaga    4920
gatatatatc atttagaaga atttatagag aagacaaaat tgaggacaaa tatgcaaggg    4980
agaattgcaa ataatgaaat taagttaatg aagcgagatt tgaaatttga agtgcaggaa    5040
ttgactaaat tctatcagat ctgttatgaa tatgtgaaat caacagaaca caaaattaaa    5100
atattcatcc ttccaaaaaa ggcttacact cccattgatt tctgctcatt agtaacaggt    5160
aatctgatat cagacaacaa atggatggtt gttcactatt taaaacaaat aactgtccca    5220
gcaaagaagg cacaaatagc cacatctata gatctggaaa tacaaatagc ctacgaatgt    5280
ttcaggctaa ttgcacattt tgctgatatg ttcctaaatg atgactccaa aaaagcttat    5340
attaatgcaa ttattaacac atatacatac aaggatgttc aagtatccag tctctacaag    5400
aaaatcaaaa attcgagact acgttcaaaa attataccat tattatatca cctgggcgat    5460
ttgcaacaaa tagacgttga cagatttgat gcagaaaaag cagaagagca gatcacatgg    5520
aataactggc aaacatctcg agaatttact actggtccaa ttgatctatc aatcaaaggt    5580
tatggacggt caataaggat cgtaggtgag gacaacaagc ttacagctgc agaaatgcaa    5640
ttgtcaagag tgagaagtga tatagtatca aggcatggac aggctttatt gaacaaacct    5700
catgggctaa aattagagaa atggaaccca gtgactgatc taaatcctaa attatggtat    5760
attgcatacc aattgcgtga gaaaaagcgg tatcactatg gggtctttag tacatcttat    5820
atagaagagc ataactcaag gatagaagca tctcggatac gtaagactaa taaatggata    5880
ccagtttgcc ctattgctat atcaaaacaa tcatctgatg gaaagcctag tcttgcaaaa    5940
atccctatgt taaatattgg ggagattaaa tttacaaaac tacagattgc agtagatgat    6000
catgcaatga ttaggaaagc cccatttagt aagatggtgt tctttgatgg cccacccata    6060
cagagcggtg gcattgacat tggaaagctt atgaagaacc aaaatattct caatttgagg    6120
ttagataata tacagagtat aacattatta gatttgtgcc gcatattttc atgccgaggg    6180
tctaaagtgg atcaagatgc atttgaattc ttatctgatg aacctttgga tgaagatgtt    6240
attgatgaat tagatagctc acctgcatta gtggtatctt acacaaagaa atcaaccaaa    6300
tccaatagtt tcaaaaatgt tatagttaga gcattgataa gagaatgtga tatatttgaa    6360
gatataatgg acataacaga cgatggattc acatctgata gcaatctaga ggtgttagaa    6420
aacttaacat ggattttaaa tatgctcgca acaaatcagt ggtctacaga actgttagca    6480
tgcatacaca tgtgtttata tcgcaatgag atggatcata tctatcacaa ttttcaagtt    6540
ccagaaatat ttgtcgacaa tccaatctca ttaaatgtaa agtgggatga agtaattatg    6600
ttcttaaaca tactgcgaga cagagattac aaatttgagc catgggtgtc tatactgaat    6660
cattccttaa ctaaagctat agagtatgct tacaaaaaga tggaagagga gaggaagcag    6720
aaatcaacag gcatcaacaa attcttaaag ggtaaaaaaa tgggtggcag atcaaagttt    6780
gatttccagt agcttgatct taaataatac ataatctttg ccccaaatct gtattatata    6840
aataattcta aagtagtttc atgtaattag gggcacacta ct                      6882
```

<210> SEQ ID NO 4
<211> LENGTH: 839
<212> TYPE: RNA
<213> ORGANISM: Schmallenberg virus

<400> SEQUENCE: 4

| | | | | | |
|---|---|---|---|---|---|
| aguaguguuc | uccacuuauu | aacuaucuua | acagaagccu | ugcaguauaa | uggugugcaa | 60 |
| uacauagaca | uauugcacgg | aaauugaaga | ucugugauga | agagguuuag | auguugauac | 120 |
| cgaauugcug | caagaagguu | cuagcagcag | gagagaaucc | agauuggcc | caggcaagcu | 180 |
| guccaacaga | auuaaaagca | gcuuuuauuu | cuguuauuuu | cugagucauc | cauucuucag | 240 |
| cagucauugu | uccauagcgu | uggcggagga | cuuuuucau | aaaauuuaca | uccauauugu | 300 |
| ccuugaggac | ccuaugcauu | ucaauaacua | guggauagaa | gucaaaagca | ucaaggaaca | 360 |
| uuucggcccc | aggugcaaau | ccaagauaca | uuguauaacc | aucggcccag | gugcauccccu | 420 |
| uaaccucagc | aagggcaug | acaaucugag | cacuagcuuc | agcaguuug | aggacacuag | 480 |
| ccuugcaugu | aucagcaauc | caacgugcua | gauauccuga | cauccuguga | aguguaaugg | 540 |
| cauugucugg | cacaggauuu | gagacauauu | ggggaaaaug | guuauuaacc | acuguaaauu | 600 |
| ugaccccacc | aaaaguaaga | ucgacacuug | guugugccgu | cuuauguagg | accaucuugg | 660 |
| ccuucuucug | guugaggaag | aagacucuag | caacaccgaa | guugaguugu | ugcccauacu | 720 |
| uaccaauaaa | ugccacauac | ccgaccuccg | gguuaaaugu | agcugcauuc | cguugggua | 780 |
| caucuucaaa | aaugaauugg | cuugacauau | uucuguaguu | aauagggag | cucacuacu | 839 |

<210> SEQ ID NO 5
<211> LENGTH: 4373
<212> TYPE: RNA
<213> ORGANISM: Schmallenberg virus

<400> SEQUENCE: 5

| | | | | | |
|---|---|---|---|---|---|
| aguaguguuc | uaccacauga | aaaacuucuc | agcugaauaa | uuacauauau | auguguaacc | 60 |
| acauauauau | guuguuauuu | guuuaucuuu | uauuguuuu | auuuauucau | uuauaauugc | 120 |
| ucauuguuau | aaggcuuauc | acuuaaauuu | auuuuccauu | ugguauauuc | ucucauugua | 180 |
| uuccaauaaa | ccuuuuagcc | guuugcacag | ugguauaau | auguauagaa | acagaauuag | 240 |
| cauaaucaaa | gagauuauua | uauauauugu | cagucuccaa | uagaaagaua | gguugccaaa | 300 |
| uagaggcuga | aauauuacgc | uaaucccuuc | uuuauaaacu | cugcaaagcc | auguagaaca | 360 |
| cuuuuuauca | uguugcucga | uguaagaugu | ucaucuaag | gaauucaaaa | caauuuuugg | 420 |
| uugauuuuua | gauauugaag | guuugugua | agcagaagcu | gagcacacac | uuacugaaac | 480 |
| ugucucuguu | gcuagugggc | aguuuaacuu | aauggaauac | ucgcucugca | ucggaucgac | 540 |
| ugcuauuauu | uuaauguaug | uaucgcaguu | acuuuuauu | gaacaaucccc | cgaugguauu | 600 |
| gguacucaau | uugagugcgc | aagccauucc | uucagggcag | ccauaacaac | caccacaccu | 660 |
| gaucucaucu | auugugacug | uugcuugugu | ugaauaugca | uguagucaa | aaucccccuaa | 720 |
| cauaauuuua | uaauugauug | uacccacgcu | ugaaacuuuu | uaugcacuu | ccauaugacu | 780 |
| gguagaagca | auaguaaug | uauuaucuug | uccaagaga | agacaagacu | gauaugaguu | 840 |
| aucaaagcau | cuucgaagga | ugacaucuuu | acgauugaau | gcauggcaaa | cauaaucaaa | 900 |
| uuuuggggu | cccgauccaa | ugacccuuc | agaauauaau | uggacugagc | cacauuucuu | 960 |
| ugcugucgaa | ccuaagucau | ugauaucccc | aacauaaacu | uucccauucu | ugacugcaau | 1020 |
| uauauuuggc | auagaguccaa | uuugaaucgu | uuggauaucu | aauuguaucc | ugucgcuaau | 1080 |

```
uaaagguugg agaacaucaa cgguacugca gaaugauuca ugggccaugg uuauacaaac    1140
uucaacaucc uuuuguucaa uacuagacuu cuuguauauc uuauauucag gccuuauuau    1200
gucuugacau gacccauaua aacaaccauc auuuauugcc aagcaacccc auucuucaca    1260
gccccaauua cuugaucuuu ccuuugagaa ugugacccaa ccaucuugau gugguauugg    1320
gcuugggcac uucccgguac auaccucuuc gugcuuggca uuuauccaa uguggguccc   1380 uguuucauau agaaaucgau acgaugcuuu auuuauuacu cuucugacau agauaauaau    1440
ggaaaagagg cuucuccau uuggcauggc aauauuaauc ccugcugaua aaccauuaau    1500
ugcagggaug ugcgacucga uauaacuauu ucuaauacca uuugauaccu guccccauu    1560 caaugucauu guuuuguauu gaggaauuau ugcuggaagg uuuuuaaug guuuaaagua    1620 gugcauaguu aaaucauuug caauaucuga cugaagcgcu gcauguagu uuucaauauc    1680 uggaugauua auagauuuag guguuaauuu auuucgauaa cuuguauccc auacuauauc    1740
ugaacaacua cuggaucuga augcauaacg caaguccagg caauuugcug auaaacagua    1800
caguguuaua ucguuaguuu ucgaauggc uuuagcugaa acauaguaaa auaagccauu    1860
ugagcauucu gcaauuugcc auugaugacc ccuacauua caugauccaa aucucuucac    1920
guugcaugau gguauuccag acuauauagg cgauucgaa uaagcauau cacuuacuuu    1980 gcauauuuuu guaguauug uccuucugc uggucaaac aucucuaggc aaugugugc    2040 acugcugcag gcuuguugcu ggucucuauu auguuguau accccaaag auggccacuu    2100 auacaucuua gauuugcaug auauauaauc uccggggugu gugacaccac guggugagua    2160
gcauaccacu uuuugggggu auuugcauac caguauggu uuggaccug aucuuuug    2220 auccaaguuu cuguggcuc cuuuuaucaa agauaaugua guuaauguuu gaggguuuu    2280 uucuauugc acguuugcac caaggauaaa aucaacaaau uccagaaauc cuuuaaguug    2340
uaaauuugac ugcgauuuag gagaaagcuu accuuguaug uggcguaaag cuggauaguc    2400
uuuuguuugu uugauuugau caagcaagac ucgaccuaau ccaggacuaa uauaucucau    2460
uauauucaau auuauuuuca ugucaugcuc aaagcgaucu ggaugaccau cauaauauau    2520
ugacauuucc cuagcguggu cugucuuggu ugaugugcac auuugcauag acuccaagca    2580
ucuacauaua uguuuaugag gauucguauu gcacacuccu aaggugaaac uucgggccag    2640
ugcuuuccau uguauguuac uugcugaauu gauagugaaa auaucaugca cuuggagagg    2700
gcacaacugu gauuuuauau acucauaaua aacuugaguc ucaauaacac uagauucgga    2760
aauaaaccua ucuaugacau uacaguucaa guuuaaacuu uuuauuaauu cuuguucguc    2820
uacugaagca ucugaaauua uuucauugau uacaacuggu gagcuuguuu uauuuugaua    2880
aaaugccaug cacuuacuca ggugcucuau uguaagcuga guugauugaa uguuuuugca    2940
guuaauacua guucuugcg ucauuacaau uguuggggacu aacagaagca uaaagauuau    3000
caacccgguc cuauuauaac uugauucaaa uuugaacaga cauuucucag aggcucugug    3060
aauuguuaag cccuuguuuu cugcgcauac acaacuuagg cacuuguuug uaaguuguc    3120 cauuaucuuc aauccacguc guucauguac cauaccacaa aagcugcagu ugcaguacaa    3180
gauauacuuu gcugccuuuu uaaguaauau uaacacaauu augcauguac aggaauauau    3240
aaagcuauau gugucaucaa uugucaagcu uuugauauua gcuagcucuc uuuuacaugu    3300
aauauacucg ucuggcaguu uuucuauauc gauacauuga cucgauauag gugugauaaa    3360
ugagaaaaau aucagugaug uuucacaca uagcacauaua uggauauuu acuuuuaca    3420 caauuuccuu guuuucggca augcuuuaua gccagaacaa uuguuacaca ugcgaugcaa    3480
```

```
uuugagugau ucaguggauag uguaaaucau uccacagaug caugucgaug ggcaauuugu    3540
aaagggaugu acugcuaaca ggcaauuuuu acacaauuua aaauauuugu uguacauaua    3600
agcauauaau uucacaaaug gauaaaauau aggaaugaac acauauacua uauauguuuu    3660
cgucaauauc aucaucauga cagacccaac uaauaugaaa guuacuagca guauuaauuc    3720
aagauucgua caaaaugauu cgaucaucaa uccggcaggu uugauccuu uaaaauagcg     3780 ggugcaugac uuuaggguau ggaaacaugc augaaaauua aguuuuuua uccacaugu     3840 uaccucaaug gauucgcaug cguuuuccaa aggaaucuca auuuguuuu uaaaccaacc    3900 ugauacaugc auugugcccg agauucggua ugguuaauu cgauaugaau ucaauauaac    3960
uucgccagua ucuuuauuca gugcuauuuc gcauucaacu cugcaugau gcauuuuagg    4020 gauuaaugug ccaguauuau cuauaucuaa uaucauaaag gaaccguggu caucauaaau    4080
uggauugcaa gaaugccaau ccuucaccug auauaaacga uaauauuua uuacagcagc    4140 caaccgaucu ccugauuuau aauguucagc auuugauuua augauagaua ugucgucuuu    4200
cacacagcau ucugaaacga ccuuugaugu guuaacaguu uuaaccaguu cgccauucag    4260
gaagcaccua gacccucuag ugccuuccuu aagugggagu gcaaaagcua aacaggcuaa    4320
guuagauauc aagacaaugu ugagaagcau uugauugug guaguucacu acu          4373
```

<210> SEQ ID NO 6
<211> LENGTH: 6882
<212> TYPE: RNA
<213> ORGANISM: Schmallenberg virus

<400> SEQUENCE: 6

```
aguagugugc cccuaauuac augaaacuac uuuagaauua uuuauauaau acagauuugg     60
ggcaaagauu auguauuauu uaagaucaag cuacuggaaa ucaaacuuug aucugccacc    120
cauuuuuuua cccuuuaaga auuuguugau gccuguugau uucugcuucc ucuccucuuc    180
caucuuuuug uaagcauacu cuauagcuuu aguuaaggaa ugauucagua uagacaccca    240
uggcucaaau uuguaaucuc ugucucgcag uauguuuaag aacauaauua cuucauccca    300
cuuuacauuu aaugagauug gauugucgac aaauauuucu ggaacuugaa aauugugaua    360
gauaugaucc aucucaugc gauauaaaca caugugu caugcuaaca guucuguaga    420
ccacugauuu guugcgagca uauuuaaaau ccauguaag uuuucuaaca ccucuagauu     480
gcuaucagau gugaaaccau cgucuguuau guccauuaua ucuucaaaua uaucacauuc    540
ucuuaucaau gcucuaacua uaacauuuuu gaaacuauug gauuugguug auucuuuugu    600
guaagauacc acuaaugcag gugagcuauc uaauucauca auaacaucuu cauccaaagg    660
uucaucagau aagaauucaa augcaucuug uccacuuuua gacccucggc augaaaauau    720
gcggcacaaa ucuaauaaug uuauacucug uauauuaucu aaccucaaau ugagaauauu    780
uugguucuuc auaagcuuuc caagucaauu gccaccgcuc uguaugggug ggccaucaaa    840
gaacaccauc uuacuaaaug gggcuuuccu aaucauugca ugaucaucua cugcaaucug    900
uaguuuugua aauuuaaucu ccccaauauu uaacauaggg auuuuugcaa gacuaggcuu    960
uccaucagau gauuguuuug auauagcaau agggcaaacu gguauccauu uauuagucuu   1020
acguauccga gaugcuucua uccuugaguu augcucuucu auauaagaug uacuaaagac   1080
cccauaguga uaccgcuuuu ucucacgcaa ugguaugca auauaccaua auuuaggauu    1140
uagaucaguc acugguucca uuucucuaaa uuuuagccca ugagguuugu ucaauaaagc   1200
```

-continued

| | |
|---|---|
| cguccaugc cuugauacua uaucacuucu cacucuugac aauugcauuu cugcagcugu | 1260 |
| aagcuuguug uccucaccua cgauccuuau ugaccgucca uaaccuuuga uugauagauc | 1320 |
| aauuggacca guaguaaauu cucgagaugu ugccaguua uuccauguga ucugcucuuc | 1380 |
| ugcuuuuucu gcaucaaauc ugucaacguc uauuuguugc aaaucgccca ggugauauaa | 1440 |
| uaaugguaua auuuugaac guagucucga auuuugauu ucuuguaga acuggauac | 1500 |
| uugaacaucc uuguauguau auguguuaau aauugcauua auauaagcuu uuuggaguc | 1560 |
| aucauuuagg aacauaucag caaaaugugc aauuagccug aaacauucgu aggcuauuug | 1620 |
| uauuuccaga ucuauagaug uggcuauuug ugccuucuuu gcgggacag uuauuuguuu | 1680 |
| uaaauaguga acaaccaucc auuuguuguc ugauaucaga uuaccuguua cuaaugagca | 1740 |
| gaaaucaaug ggaguguaag ccuuuuugg aaggaugaau auuuaauuu uguuucugu | 1800 |
| ugauuucaca uauucauaac agaucugaua gaauuuaguc aauccugca cuucaaauuu | 1860 |
| caaaucucgc uucauuaacu uaauuucauu auuugcaauu cucccuugca uauuuguccu | 1920 |
| caauuuuguc uucucuauaa auucuucaa augauauaua ucucccgca uuucaucugg | 1980 |
| cuccaucccu uuuugcucau aguuaucugu uacauaagca cguaauacga gagcaggacu | 2040 |
| augauaaauu acuuuaaggc ucuuaaucuc cggcauauaa cagcauguca uacccaaucg | 2100 |
| uugcaucucc acucccugua uugaaauuaa aaguguguu gcacaagcaa cuaauauagg | 2160 |
| gucguucauu auacagaagc uauauaucgu cuuuauaucc ucuacaucaa guuaaauuu | 2220 |
| uucuacauca auuuuauuu gcugauaugu uucaacaaaa gucuucuugc caauaauaca | 2280 |
| uguagcauca uuuauauuug ggucaucuug uauaccaaac aaccuaucau gaauacuugu | 2340 |
| auagcuauc auugguuuau uugcaaacaa acuuguucu augaagagcu gagcuggguu | 2400 |
| uugaauagac aaugaauucuu uaaauuuacg acuguugau cugaacaaua cagacauaca | 2460 |
| gaacucuuca caagucucac cuuuuguaac caauaguuga ggguuggcua uaaaauauuc | 2520 |
| aaauaauucu ucaauuucu guuggucuug uauuguuuu ugauaaucag cauaugaaug | 2580 |
| caaucuagau aacgaacuug caguagugaa uuuucuuggu gucagaagag accuagaucu | 2640 |
| cauuucacua guuucgccca uuccaucauc agaugacaua guugagcua acgucaugua | 2700 |
| ucuuaaaagc uuaagucuga aaauaucaca uugugucagu uuacuuauau cccauguaug | 2760 |
| uauauucuca uauugaugcu ggauuggunc acggcaaaga uguauagggg acauucuuuu | 2820 |
| ugauaaccua acuaaauaac uuagauuauc ugcuuccaaa ccugcuauag cuauagugg | 2880 |
| uaauucugaa uuuauuaagc cacacaauuc uauaggcagc ucaaaucuau caugacuagg | 2940 |
| uaaagaugaa guaggaucau ugauuugacc uggaagcaug uuauaugugc uauguguuau | 3000 |
| ccacugaguu aaugcaauag cagcccaugc aagugaugga ggugcuccau gcuuaauugc | 3060 |
| ugucugcguu gcagacaacc uacuggcaac auccucauau gguccaagaa aagcacaauc | 3120 |
| gccaacagau gucaaauaa agcgaccaua aacagaaaau ggcucaccau aaauauuaaa | 3180 |
| aagugaaacg aacuccuuua ugaaauugu uauauaugc uucuucauau uugcuugauu | 3240 |
| uccaaaaguu agacauauuu uucaaauag uuugcagaa aauucaauaa caauaucauc | 3300 |
| aucuaauuua ucuuggauca ucacuauuga agugugauu ucaucagaau gaaccauaga | 3360 |
| auugacuaaa acuucccuu cuaguaaagu ggcugcucuc uuuagaauau ccuuauaaac | 3420 |
| auucauagaa caugaaugua gguagcuacu uguguaauug agauuccccu gcagccaguu | 3480 |
| ccguuuaaua uugaccccaau uuugcgauaa gccauugguc auuucauaua uuauaucauc | 3540 |
| cucauguuug auacguuggu caaggaugcu acagagcauu ucaucaggca gaauuagcuu | 3600 |

```
uuuuugcaua uaauugcaua ggaaguacaa uauccuuucu uuuucuugca gauaaagugc    3660
gggaucuaau gcaaacaacc agaaauauuu gaauaaaaca ucuugggcac uccauuuuga    3720
caugucugca uugauuucaa ucuuaacaga augugguuua uaugcgauca uauggcuugc    3780
uucucccauu ucugcuaaau agcguucuuu gaucuguuuu auaguugcug cugugaaucg    3840
uauuucagac ucugcaagcu cuucuaauuu uuucaauuua gaaucgccug guucacuaau    3900
caucucaucu ggauucaacu uacagcguuc uuuagauauc cuccacuua aaucaagca     3960 cauuuugcc ucaaauucgc cuacgaauau ucccuaucc uuugcuguuu uuggccuuu      4020 guuaaagaau guaaacuuaa aaucugugug auucuucaua gcagagagua uaugauacac    4080
aguggguuua ucaucuaucu ccuuccuuuu uauuuucugg uacagagaau caaauacuuu    4140
aguugacaua augucaauau aauucgggau ugcuuuuuuu aagucuucau agcgugaaug    4200
ucuuauaguu gcauuuagua acuucauc aacaaauucu ggguuugcaa uuguauacuu      4260
cuuuaucucu uuugacaugc aaucugcagc cuuuuuguu gcugagcuuu uucuuucuc      4320 aaagucgccu acuuuaauac augauuuaga gcuggugaau guagaaauag ugcauaucga    4380
ucuauuuaag uuguuugugu uuucuauccg ugaucuaaua uaauuauguc uagcagraguc    4440 cauuauuaga uuuuuugcaa cugcauagau aguuauauuu aaauuugcag uuuguuuucu    4500 aguguugua gaccauauuc cugggauauu uaaucucugg ucccuuucua uaucuaagau     4560
ugucuuagcc agaucuauca uaacaugaug cuuuucaugc aaaccuuuug aauugaagua    4620
aaaugguaga uauauuuggu uaauauauuc uuuuagugau acauagccuu caaaccagau    4680
ugaugauagg ucucuguuau cucucacacc uuuugaguu auuucauaau cuguuaggca    4740
gauauuccuc augucuacuu uaucucuuug auuauaugcc auauaacauc cccuuuuaau    4800
caaguuugcc auuacuacag agaagcuggu cuuuguauaa gggccaaauu uuucugcuau    4860
auaaucucua acaugacugg auauggcuaa ugaauucauu aucauauauc uugaugguuc    4920
ugucaaugac agcauagcuu igguuauaga cagggaagug uggaauguaa aauucaugac    4980
aucagucaaa uugagugucg gauugucccc ugcaaacauc aauguagauca acauaaaaag   5040 ucccggugaa cuaacuaugc guugacaucg uucuuuaucu aaacgcauuc cuuuagagau    5100
acuaagguau uuugaaccag uuuuuaaaugu cgcaugcaau gcaccguggu gcaucacauu    5160
cugaggagua gaaugcaaca cagcuaagaa guaaacaagu guggaucgcu ugcuuuaau     5220 aucagaagaa ggcauuacaa acccaaacag auuauuguuu gcacaacaca cuacacgaaa   5280
aguauugugc cuauuauauu gagaaacugc caacauauuu uucaucaaga cugaaaaauc    5340
uuuaauacaa gcccaguaau uugacuuccc uaucgguua aucugauccc auguauccuu     5400
ugaacaugau gcauauuuug caccauauuc uucuaaauaa cauccuauac gcucuagauu    5460
auuaucuccg auaguauuu ucuuuacauu uucauacugg aauugcaaa aaucaaugac      5520 uuccuuuuug uugaaaucua auauagagg uuugucagua ccaaaucgu caauggucuu     5580 uuugaaaau ugcacgugac ccccuaugcc aagaaaucu uuuagcaaau gugauuugc     5640 uuuuguauuc auuauuucag uaccaguuu aaacugcgu ucccaauaaa uugucgcgu      5700 gccuauuug auugguucca guuuaaguauc aauucuuuuc gauguccguc uugccauacu    5760
uuuuaguuug cuagugugug cuucauauaa agcugugguuc ucagaaaagu ccauaagcau   5820
acccaaugcu cugaaugcgc uuuauauguu agacucgcca gaaauauuuu ggagugcuuu    5880
ugcaaucuug auuaguuuug guguuguucgc auuugauguu ucgucagguu gaccccauau    5940
```

```
gaaaugaaua gauggu uuuu gcuugcugac aucuugaguc agguuucucu caguacucac    6000
ucuuugaacc auuugauucc aaccgauugu gauuucauca ugauuugguu uugggu aguu    6060
cccuucacau cuaaagauuc cugcagcggc cucuuucaca aaaauguuau aaucauugcc    6120
auaucuauuu auaaccuuuu guagauuuug auuccauuuc ucaccgcgag uugcaucaaa    6180
ugucauagac ucauggaaug ucaguuuagc caucucaucu aaagaaucau agaauuccaa    6240
aaagacaggg ugugaauaga gcuccggggu auccucauca auccaggguc cagcaucgu     6300
aaauucaccu ugauucacaa uuucuaggaa ucugucguca uccuuauauu ucucauauau    6360
cagggaucgc aaauuaaaga accaaguaaa aucaagguuu auguugagcg cccaaauau     6420
uuccaagaau ugauuugaau uaacauggau aguaucucgc agagggucag cacggaugau    6480
cacaacuuca aaaucaaacg gcaauucuga caaugcgucu ccaaagaucu ggguguacuu    6540
uucauaaguu uuuugaccau augcaugauc aguugauacu uuauagucaa ugauauaaag    6600
cuugccauug ugaaugauaa aauugucugg uguacaauug cgaauguuga aagcagugcc    6660
agcuggcaga aauucaagaa guaugucgua agcuggaaca uccugccgga auucgauauc    6720
cagguaauaa cauaccucuc uaccaaagua gucaugucua gccaugagaa gaucagcaac    6780
aaugucuuug gcuucuucag cacuucgaca cugguugauc cuaucucuaa aaauguuaau    6840
cuuguauguc uccauaguga uuguaauuag ggguacacua cu                       6882
```

```
<210> SEQ ID NO 7
<211> LENGTH: 839
<212> TYPE: DNA
<213> ORGANISM: Schmallenberg virus

<400> SEQUENCE: 7
```

```
agtagtgaac tccactatta actacagaaa tatgtcaagc caattcattt ttgaagatgt      60
accacaacgg aatgcagcta catttaaccc ggaggtcggg tatgtggcat ttattggtaa     120
gtatgggcaa caactcaact tcggtgttgc tagagtcttc ttcctcaacc agaagaaggc     180
caagatggtc ctacataaga cggcacaacc aagtgtcgat cttactttg gtggggtcaa      240
atttacagtg gttaataacc attttcccca atatgtctca aatcctgtgc cagacaatgc     300
cattacactt cacaggatgt caggatatct agcacgttgg attgctgata catgcaaggc     360
tagtgtcctc aaactagctg aagctagtgc tcagattgtc atgccccttg ctgaggttaa     420
gggatgcacc tgggccgatg gttatacaat gtatcttgga tttgcacctg ggccgaaat      480
gttccttgat gcttttgact tctatccact agttattgaa atgcataggg tcctcaagga     540
caatatggat gtaaatttta tgaaaaagt cctccgccaa cgctatggaa caatgactgc      600
tgaagaatgg atgactcaga aataacaga ataaaagct gcttttaatt ctgttggaca       660
gcttgcctgg gccaaatctg gattctctcc tgctgctaga accttcttgc agcaattcgg    720
tatcaacatc taaaccctctt catcacagat cttcaatttc cgtgcaatat gtctatgtat    780
tgcacaccat tatactgcaa ggcttctgtt aagatagtta ataagtggag aacactact    839
```

```
<210> SEQ ID NO 8
<211> LENGTH: 839
<212> TYPE: RNA
<213> ORGANISM: Schmallenberg virus

<400> SEQUENCE: 8
```

```
aguaguguuc uccacuuauu aacuaucuua acagaagccu ugcaguauaa uggugugcaa     60
uacauagaca uauugcacgg aaauugaaga ucgugauga agagguuuag auguugauac     120
```

```
cgaauugcug caagaagguu cuagcagcag gagagaaucc agauuuggcc caggcaagcu      180
guccaacaga auuaaaagca gcuuuuauuu cuguuauuuu cugagucauc cauucuucag      240
cagucauugu uccauagcgu uggcggagga cuuuuuucau aaaauuuaca uccauauugu      300
ccuugaggac ccuaugcauu ucaauaacua guggauagaa gucaaaagca ucaaggaaca      360
uuucggcccc aggugcaaau ccaagauaca uuguauaacc aucggcccag gugcaucccu      420
uaaccucagc aaggggcaug acaaucgag cacuagcuuc agcuaguuug aggacacuag       480
ccuugcaugu aucagcaauc caacgugcua gauauccuga cauccuguga aguguaaugg      540
cauugucugg cacaggauuu gagacauauu ggggaaaaug guuauuaacc acuguaaauu      600
ugaccccacc aaaaguaaga ucgacacuug guugugccgu cuuauguagg accaucuugg     660
ccuucuucug guugaggaag aagacucuag caacaccgaa guugaguugu ugcccauacu     720
uaccaauaaa ugccacauac ccgaccuccg gguuaaaugu agcugcauuc cguugguggua    780 caucuucaaa aaugaauugg cuugacauau uucuguaguu aauaguggag uucacuacu      839
```

SCHMALLENBERG VIRUS (SBV) VACCINE, METHODS OF PRODUCTION, AND USES THEREOF

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

1. Technical Field

The present invention belongs to the field of vaccines and medicaments for the prophylaxis and treatment of infectious diseases. In particular, it relates to inactivated viruses useful as vaccine or medicament for preventing or treating viremia, the transmission and clinical symptoms, in particular malformations in newborn ruminants such as cattle, sheep and goats, induced by Schmallenberg virus.

2. Background Information

A novel orthobunyavirus, the Schmallenberg virus (SBV), was discovered in Europe in November 2011. After the first detection, the reported cases of SBV in sheep, cattle, and goats dramatically accumulated in several European countries to several thousand cases of PCR-positive malformed lambs and calves (1, 2). The virus was detected by metagenomics at the Friedrich-Loeffler-Institut (FLI) in samples of cattle with milk drop and fever. The investigated samples were collected in a farm near the city of Schmallenberg (North Rhine-Westphalia, Germany), and consequently the virus was named Schmallenberg virus (SBV). SBV is a member of the genus Orthobunyavirus within the family Bunyaviridae. It is related to the so-called Simbu serogroup viruses (1).

Orthobunyaviruses have a segmented, negative stranded RNA genome and are mainly transmitted by insect vectors like midges and mosquitos. The three segments (S, M and L) of the Orthobunyavirus genome allow genetic reassortment, which naturally occurs resulting in the emergence of viruses with new biological properties (3). The largest segment L encodes the RNA-dependent RNA polymerase. The M-segments encodes the viral surface glycoproteins Gn and Gc which are responsible for cell fusion, viral attachment and the induction of neutralizing antibodies. The small S-segment encodes the nucleocapsid N which is also involved in complement fixation (4). The relationship between Orthobunyaviruses was often only determined by serological cross-reactivity (5). In the era of DNA sequencing, phylogenetics has additionally been assessed by comparison of partial genome sequences (full N and partial Gc gene) (6). Therefore, available and published genome sequence information of full-length genomes is sparse. As a consequence, in-depth phylogenetic analyses are difficult. In conclusion, a detailed and reliable taxonomic classification of SBV could not be made. Preliminary investigations showed similarities of the M- and L-segment sequences to partial AKAV and Aino virus (AINOV) sequences. The N gene was most closely related to Shamonda virus (SHAV) (1).

SBV is like Akabane virus (AKAV) able to cross the placental barrier in pregnant cows and sheep, infect the fetus and cause fatal congenital defects during a susceptible stage in pregnancy (2). The Simbu serogroup, named after the prototype virus, is the largest serogroup of Orthobunyavirus and contains at least 25 viruses, among them medically important viruses such as Akabane virus, Oropouche virus, Sathuperi virus or Douglas virus, most of which can cause malformations in new born ruminants, but also human beings can be affected. Akabane virus, for instance, causes congenital defects in ruminants and circulates in Asia, Oceania and Africa, whereas Oropouche virus is responsible for large epidemics of Oropouche fever, a zoonosis similar to dengue fever, in human populations in South America. Sathuperi virus has lent his name to the Sathuperi serogroup, to which belong also Douglas virus and SBV.

SBV was the first orthobunyavirus of the Simbu serogroup detected in Europe. The virus is apparently transmitted by arthropod vectors. Biting midges probably play an important role in transmission. According to the current state of knowledge, ruminants are susceptible to infection with SBV. Adult animals may develop mild disease, if any. However, transplacental infection occurs frequently and can lead to severe congenital malformation of the vertebral column (Kyphosis, lordosis, scoliosis, torticollis) and of the scull (macrocephaly, brachygnathia inferior) as well as variable malformations of the brain (hydracephaly, porencephaly, cerebellar hypoplasia, hypoplasia of the brain stem) and of the spinal cord in lambs, kids and calves. The infection spread rapidly over large parts of North Western Europe. Belgium, Germany, France, Italy, Luxembourg, the Netherlands, Spain and the United Kingdom have been affected so far.

Therefore, SBV is a serious threat to ruminant livestock in Europe since vaccines are currently not available.

Thus, there is a strong need for vaccines and medications effecting a rapid induction of neutralizing antibodies for the prophylaxis and treatment of Schmallenberg virus infection.

DESCRIPTION OF THE INVENTION

The solution to the above technical problem is achieved by the description and the embodiments characterized in the claims.

Thus, the invention in its different aspects is implemented according to the claims.

In one aspect, the invention provides an immunogenic composition containing one or more antigens of the Schmallenberg virus (SBV), wherein the immunogenic composition preferably comprises the SBV.

Preferably, SBV is thus contained as the one or more antigens of SBV in the composition of the invention, or the one or more antigens of the SBV is/are preferably SBV, respectively. Hence, the immunogenic composition of the invention is in particular an immunogenic composition comprising Schmallenberg virus (SBV).

As used herein, the term "antigen" in particular refers to any molecule, moiety or entity capable of eliciting an immune response. This includes cellular and/or humoral immune responses. Depending on the intended function of the composition, one or more antigens may be included be included.

In a further preferred aspect, the antigen of SBV or the SBV contained in the immunogenic composition of the invention is inactivated.

According to one aspect, the immunogenic composition of the invention is thus preferably an immunogenic composition comprising inactivated Schmallenberg virus (SBV).

The term "inactivated", as used herein, means that the antigen does not cause disease, when administered to a mammalian host or does not replicate in a host cell.

The invention also provides an immunogenic composition comprising SBV or an antigen of SBV, wherein the SBV comprises
 a small (S) RNA segment having a sequence that is inverse complementary to a nucleic acid sequence having at least 97.8%, preferably at least 99% sequence identity with the nucleic acid sequence of SEQ ID NO:1 or SEQ ID NO:7, a medium (M) RNA segment having a sequence that is inverse complementary to a nucleic acid sequence having at least 82.2% sequence identity with the nucleic acid sequence of SEQ ID NO:2, and/or a large (L) RNA segment having a sequence that is inverse complementary to a nucleic acid sequence having at least 93% sequence identity with the nucleic acid sequence of SEQ ID NO:3.

Preferably, said SBV comprises said small (S) RNA segment, said medium (M) RNA segment and said (L) RNA segment.

According to another aspect, the SBV or the antigen of the SBV is obtainable by the inactivation of SBV or the antigen of SBV, wherein said SBV comprises a small (S) RNA segment having a sequence that is inverse complementary to a nucleic acid sequence having at least 97.8%, preferably at least 99% sequence identity with the nucleic acid sequence of SEQ ID NO:1 or SEQ ID NO:7, a medium (M) RNA segment having a sequence that is inverse complementary to a nucleic acid sequence having at least 82.2% sequence identity with the nucleic acid sequence of SEQ ID NO:2, and/or a large (L) RNA segment having a sequence that is inverse complementary to a nucleic acid sequence having at least 93% sequence identity with the nucleic acid sequence of SEQ ID NO:3.

All sequences of the sequence listing are typed in 5'-'3 direction. The sequences of SEQ ID NOs.1 to 3 and 7 code for cDNAs having a positive polarity (+ strand). The term "inverse complementary" means that the sequence is antiparallel to the reference sequence.

Preferably said SBV comprises said small (S) RNA segment, said medium (M) RNA segment and said (L) RNA segment.

It is understood that the term "RNA segment", as used herein, is equivalent to "genome segment" or "segment", as frequently used in the context of Schmallenberg virus.

Preferably, the small (S) RNA segment mentioned herein has an RNA sequence that is inverse complementary to a DNA sequence having at least 97.8%, more preferably at least 98.5%, even more preferably at least 99%, still more preferably at least 99.5% or in particular 100% sequence identity with the nucleic acid sequence of SEQ ID NO:1, or preferably, the small (S) RNA segment described herein has an RNA sequence that is inverse complementary to a DNA sequence having at least 97.8%, more preferably at least 98.5%, even more preferably at least 99%, still more preferably at least 99.5% or in particular 100% sequence identity with the nucleic acid sequence of SEQ ID NO:7.

Preferably, the medium (M) RNA segment mentioned herein has an RNA sequence that is inverse complementary to a DNA sequence having at least 83%, more preferably at least 85%, even more preferably at least 90%, still more preferably at least 95% or in particular 100% sequence identity with the nucleic acid sequence of SEQ ID NO:2.

Preferably, the large (L) RNA segment mentioned herein has an RNA sequence that is inverse complementary to a DNA sequence having at least 94%, more preferably at least 96%, still more preferably at least 98% or in particular 100% sequence identity with the nucleic acid sequence of SEQ ID NO:3.

As used herein, the term "immunogenic composition" in particular refers to a composition that will elicit an immune response in a mammal and/or an insect that has been exposed to the composition. An immune response may include induction of antibodies and/or induction of a T-cell response.

Sequence identity in the context of the invention is understood as being based on pairwise sequence alignments. For purposes of the present invention, pairwise sequence alignments are done with ClustalW as implemented in Mega5 (K. Tamura et. al., MEGA5: Molecular Evolutionary Genetics Analysis using Maximum Likelihood, Evolutionary Distance, and Maximum Parsimony Methods. Mol. Biol. Evol. 28, 2731-2739 (2011)), using the default settings (gap opening penalty of 15 and gap extension penalty of 6.66; DNA weight matrix: ClustalW 1.6; Transition weight of 0.5). Sequence identities of the aligned sequences are calculated using BioEdit version 7.0.9.0.

It is understood that the term "sequence identity to", as used herein, herein, is equivalent to the term "sequence identity with the nucleic acid sequence of". Thus, as mentioned herein, the term "sequence identity to SEQ ID NO:4 or SEQ ID NO:8" is equivalent to the term "sequence identity with the nucleic acid sequence of SEQ ID NO:4 or SEQ ID NO:8", the term "sequence identity to SEQ ID NO:5" is equivalent to the term "sequence identity with the nucleic acid sequence of SEQ ID NO:5", and the term "sequence identity to SEQ ID NO:6" is equivalent to the term "sequence identity with the nucleic acid sequence of SEQ ID NO:6".

As used herein, it is in particular understood that the term "sequence identity with the nucleic acid sequence of SEQ ID NO:X" is equivalent to the term "sequence identity with the nucleic acid sequence of SEQ ID NO:X over the length of SEQ ID NO: X" or to the term "sequence identity with the nucleic acid sequence of SEQ ID NO:X over the whole length of SEQ ID NO: X", respectively. In this context, "X" is any integer selected from 1 to 8 so that "SEQ ID NO: X" represents any of the SEQ ID NOs mentioned herein.

In a further preferred aspect of the invention, the SBV mentioned herein comprises an S RNA segment, characterized in that the S RNA segment has a sequence having at least 97.8%, preferably at least 99% sequence identity to SEQ ID NO:4 or SEQ ID NO:8, an M RNA segment, characterized in that the M RNA segment has a sequence having at least 82.2% sequence identity to SEQ ID NO:5, and/or an L RNA segment, characterized in that the L RNA segment has a sequence having at least 93% sequence identity to SEQ ID NO:6, and wherein in particular said SBV comprises said small (S) RNA segment, said medium (M) RNA segment and said (L) RNA segment.

Preferably, the SBV mentioned herein comprises an S RNA segment, characterized in that the S RNA segment has an RNA sequence having at least 97.8%, more preferably at least 98.5%, even more preferably at least 99%, still more preferably at least 99.5% or in particular 100% sequence identity to SEQ ID NO:4, or an RNA sequence having at least 97.8%, more preferably at least 98.5%, even more preferably at least 99%, still more preferably at least 99.5% or in particular 100% sequence identity to SEQ ID NO:8; and/or an M RNA segment, characterized in that the M RNA segment has a RNA sequence having at least 83%, more preferably at least 85%, even more preferably at least 90%, still more preferably at least 95% or in particular 100% sequence identity to SEQ ID NO:5; and/or an L RNA segment, characterized in that the L RNA segment has a RNA sequence having at least 94%, more preferably at least 96%, still more preferably at least 98% or in particular 100% sequence identity to SEQ ID NO:6.

The term "having 100% sequence identity", as used herein, is also understood to be equivalent to the term "being identical".

Preferably, the inactivated SBV is obtainable by the inactivation of SBV by heat treatment or preferably with a virus inactivating agent, wherein in particular an aziridine compound, most preferably binary ethyleneimine (BEI), is used for the inactivation.

According to one preferred aspect, BEI is added to the antigen in a final concentration of 10 mM or less, wherein it has been surprisingly found that a final concentration of less than 4 mM is sufficient for the inactivation of the antigen. Thus, BEI is preferably added to a final concentration of less than 4 mM to the antigen, more preferably to a final concentration of 0.5 to 3.5 mM, most preferably to a final concentration of 1 to 3 mM.

After the addition of BEI, the mixture is preferably kept in agitation for 48 h or less, preferably for 24 h or less, most preferably for between 6 h and 18 h, such as e.g. for 12 h. The temperature of the mixture while the mixture is being agitated is preferably 37+/−5° C., most preferably 37+/−1° C.

Further, it has been found that only one inactivation step, e.g. by adding BEI to the antigen, is sufficient for the inactivation of the antigen.

After the inactivation procedure, the residual virus inactivating agent is preferably neutralized by adding a neutralizing agent to the mixture, in particular in a molar excess in comparison to the amount of virus inactivating agent added to the antigen. If an aziridine compound is used for the inactivation, then preferably a nucleophile which opens the three-membered ring is used for the neutralization. BEI is preferably neutralized by the addition of sodium thiosulphate, in particular in a 1.1 to 10 fold molar excess, most preferably in a 2 to 8 fold molar excess in comparison to the amount of BEI added to the antigen.

In a preferred aspect, the immunogenic composition of the invention comprises an amount of SBV which is equivalent to a virus titre of at least about $10^5$ $TCID_{50}$/mL per dose, preferably between $10^5$ to $10^7$ $TCID_{50}$/mL per dose, more preferably about $10^6$ $TCID_{50}$/mL per dose.

Surprisingly, it has been found that an immunogenic composition of the invention comprising an amount of SBV which is equivalent to a virus titre of less than $10^{5.5}$ $TCID_{50}$/ml per dose, preferably less than $10^5$ $TCID_{50}$/ml per dose, is sufficient to prevent SBV RNAemia in an animal, in particular in sheep.

Thus, the immunogenic composition of the invention preferably comprises an amount of SBV which is equivalent to a virus titre of less than $10^{5.5}$ $TCID_{50}$/ml per dose, preferably less than $10^5$ $TCID_{50}$/ml per dose, more preferably between $10^3$ to $10^5$ $TCID_{50}$/mL per dose, most preferably between $10^4$ to $10^5$ $TCID_{50}$/mL per dose, in particular for use in a method for inducing an immune response against SBV and/or for preventing or reducing viremia or malformations induced by SBV and/or for preventing or reducing the transmission of SBV, preferably in sheep.

"RNAemia" as described herein is in particular understood as the detection of RNA (e.g., by nucleic acid sequence-based amplification or reverse transcription PCR) in a sample of an animal, in particular in samples of plasma, serum or whole blood.

It is thus in particular understood, according to the invention, that viremia induced by SBV goes hand in hand or is accompanied, respectively, with SBV RNAemia in a sample of blood serum of an animal. Hence, viremia induced by SBV can be examined by detecting specific SBV RNA in the serum of animals.

In another preferred aspect, the immunogenic composition of the invention contains SBV having a pre-inactivation titre of at least about $10^6$ SBV particles per milliliter, preferably between $10^6$ to $10^8$ $TCID_{50}$/mL SBV particles per milliliter, more preferably about $10^7$ SBV particles per milliliter.

The term "pre-inactivation titre", as used herein, in particular refers to the amount of suspended SBV which is inactivated.

In particular, the immunogenic composition of the invention, further contains one or more pharmaceutically acceptable carriers or excipients, wherein said one or more pharmaceutically acceptable carriers or excipients are preferably selected from the group consisting of solvents, dispersion media, adjuvants, stabilizing agents, diluents, preservatives, antibacterial and antifungal agents, isotonic agents, and adsorption delaying agents.

In a particular preferred aspect, the immunogenic composition of the invention further contains one or more adjuvants, preferably aluminium hydroxide and/or saponin, e.g. Alhydrogel and/or Quil-A, wherein a combination of aluminium hydroxide and saponin is most preferred.

Another aspect concerns the immunogenic composition of the invention for use as a medicament, preferably as a vaccine.

A further aspect relates to the immunogenic composition of the invention for use in a method for inducing an immune response against SBV and/or for preventing or reducing viremia or malformations induced by SBV and/or for preventing or reducing the transmission of SBV.

This aspect in particular relates to the immunogenic composition of the invention for use in a method for inducing an immune response against SBV in a ruminant and/or insect and/or for preventing or reducing viremia in a ruminant and/or insect and/or for preventing or reducing malformations induced by SBV in a ruminant fetus or newborn and/or for preventing or reducing the transmission of SBV by arthropod vectors, preferably insects and/or for preventing or reducing the transmission of SBV from the pregnant animal (the mother) to the fetus.

As used herein, the term "inducing an immune response" to an antigen or composition is the development of a humoral and/or cellular immune response in an animal to an antigen present in the composition of interest.

The term "prevention" or "reduction" or "preventing" or "reducing", respectively, as used herein, means, but is not limited to a process which includes the administration of a SBV antigen, namely of the antigen of SBV according to the invention which is included in the composition of the invention, to an animal, wherein said SBV antigen, when administered to said animal elicits or is able to elicit an immune response in said animal against SBV. Altogether, such treatment results in reduction of the clinical signs of a disease caused by SBV or of clinical signs associated with SBV infection, respectively. More specifically, the term "prevention" or "preventing", as used herein, means generally a process of prophylaxis in which an animal is exposed to the immunogenic composition of the present invention prior to the induction or onset of the disease process caused by SBV.

Herein, "reduction of clinical signs associated with SBV infection" means, but is not limited to, reducing the number of infected subjects in a group, reducing or eliminating the number of subjects exhibiting clinical signs of infection, or reducing the severity of any clinical signs that are present in the subjects, in comparison to wild-type infection. For example, it should refer to any reduction of pathogen load, pathogen shedding, reduction in pathogen transmission, or reduction of any clinical sign symptomatic of SBV infection, in particular of the transmission of SBV from the mother to the fetus or of the malformations induced by SBV in a ruminant fetus or newborn. Preferably these clinical signs are reduced in subjects receiving the composition of the present invention by at least 10% in comparison to subjects not receiving the composition and may become infected. More preferably, clinical signs are reduced in subjects receiving the composition of the present invention by at least 20%, preferably by at least 30%, more preferably by at least 40%, and even more preferably by at least 50%.

The term "reduction of viremia induced by SBV" (or, alternatively, "reduction of RNAemia induced by SBV") means, but is not limited to, the reduction of SBV virus entering the bloodstream of an animal, wherein the viremia level, i.e. the number of SBV RNA copies per mL of blood serum or the number of plaque forming colonies per deciliter of blood serum, is reduced in the blood serum of subjects receiving the composition of the present invention by at least 50% in comparison to subjects not receiving the composition and may become infected. More preferably, the viremia level is reduced in subjects receiving the composition of the present invention by at least 90%, preferably by at least 99.9%, more preferably by at least 99.99%, and even more preferably by at least 99.999%.

As used herein, the term "viremia" is particularly understood as a condition in which Schmallenberg virus particles reproduce and circulate in the bloodstream of an animal, in particular of a mammal or of an insect.

The term "animal", as used herein, in particular relates to a mammal or to an insect.

Preferably, the mammal as mentioned herein is a ruminant. More preferably, the ruminant as mentioned herein is selected from the group consisting of cattle, sheep, goats, deer, elk, giraffes, bison, moose, yaks, water buffalo, camels, alpacas, llamas, antelope, pronghorn, and nilgai. Most preferably, the mammal or ruminant as mentioned herein is selected from the group consisting of cattle, sheep and goats.

The insect, as mentioned herein, is preferably selected from the group consisting of midges, in particular *Culicoides* spp., biting flies and mosquitoes.

Further, the invention provides a vaccine composition for the treatment or prevention of SBV or for the prevention or reduction of the viremia of malformations induced by SBV and/or for the prevention or reduction of the transmission of SBV, wherein the vaccine comprises the immunogenic composition of the invention.

In particular, the invention provides a vaccine composition, which comprises the immunogenic composition of the invention, for use in a method for inducing an immune response against SBV in a ruminant and/or insect and/or for preventing or reducing viremia in a ruminant and/or insect and/or for preventing or reducing malformations induced by SBV in a ruminant fetus or newborn and/or for preventing or reducing the transmission of SBV by arthropod vectors, preferably insects.

The term "malformations", as used herein, in particular relates to a malformation selected from congenital malformation of the vertebral column (Kyphosis, lordosis, scoliosis, torticollis) and/or of the scull (macrocephaly, brachygnathia inferior), variable malformations of the brain (hydracephaly, porencephaly, cerebellar hypoplasia, hypoplasia of the brain stem) and of the spinal cord, malformations and/or stiffening of fore and/or hind legs. More particular, the term "malformations" relates to malformations in lambs, kids and calves.

The invention also provides a method for the production of infectious SBV, comprising the steps of
  infecting cells, preferably mammalian or insect cells, with a SBV,
  cultivating the infected cells,
  harvesting the SBV produced by said cells.

The term "infecting", as used herein, in particular refers to the process of contacting cells with SBV, such as by inoculation.

Said infection of the cells with a SBV in particular includes attachment of the virus to a cell, entry of the virus into the cell, uncoating of the virion in the cytoplasm, replication and transcription of the viral genome, expression of viral proteins and assembly and release of new infectious viral particles.

The term "cultivating", as used herein, is particularly directed to the maintenance and preferably the growth of cells under suitable conditions.

The term "harvesting", as used herein, in particular refers to the taking of cell supernatant which contains viral particles, such as by centrifugation of a container containing a culture of virus infected cells and subsequent decantation of the cell supernatant.

Surprisingly, it has been found that SBV remains infectious, and thus also remains its antigenic potential, when it is alternately passaged between insect cells and mammalian cells.

Thus, the invention in particular concerns a method for the production of preferably infectious SBV, in particular the above-mentioned method, wherein the SBV is passaged alternately between insect cells and mammalian cells.

Hence, the method for the production of infectious SBV according to the invention in particular comprises the steps of:
  (a) infecting insect cells with a SBV,
  (b) cultivating the infected cells of step (a),
  (c) harvesting the SBV produced by said cells in step (b),
  (d) infecting mammalian cells with the SBV harvested in step (c),
  (e) cultivating the infected cells of step (d), and
  (f) harvesting the SBV produced by said cells in step (e)
or comprises the steps of
  (d) infecting mammalian cells with a SBV,
  (e) cultivating the infected cells of step (d),
  (f) harvesting the SBV produced by said cells in step (e)
  (g) infecting insect cells with the SBV harvested in step (f),
  (h) cultivating the infected cells of step (g), and
  (i) harvesting the SBV produced by said cells in step (h).

In this regard, the numeration of the steps (d)-(i) is equivalent to the numeration (a')-(f') and has been chosen for reasons of clarity in view of the further steps described herein (starting with the step "(j)").

Preferably, the method for the production of SBV of the invention comprises the steps of:
  (a) infecting insect cells with a SBV,
  (b) cultivating the infected cells of step (a),
  (c) harvesting the SBV produced by said cells in step (b)
  (d) infecting mammalian cells with the SBV harvested in step (c),
  (e) cultivating the infected cells of step (d),
  (f) harvesting the SBV produced by said cells in step (e)
  (g) infecting insect cells with the SBV harvested in step (f)
  (h) cultivating the infected cells of step (g), and
  (i) harvesting the SBV produced by said cells in step (h).

More preferably, the method for the production of infectious SBV according to the invention further comprises the steps of
(j) infecting mammalian cells with the SBV harvested in step (i),
(k) cultivating the infected cells of step (j), and
(l) harvesting the SBV produced by said cells in step (k), and optionally
(m) infecting insect cells with the SBV harvested in step (l),
(n) cultivating the infected cells of step (m), and
(o) harvesting the SBV produced by said cells in step (n).

Thus, in one aspect, the method for the production of infectious SBV according to the invention comprises the steps of
(a) infecting insect cells with a SBV,
(b) cultivating the infected cells of step (a),
(c) harvesting the SBV produced by said cells in step (b)
(d) infecting mammalian cells with the SBV harvested in step (c),
(e) cultivating the infected cells of step (d),
(f) harvesting the SBV produced by said cells in step (e)
(g) infecting insect cells with the SBV harvested in step (f)
(h) cultivating the infected cells of step (g),
(i) harvesting the SBV produced by said cells in step (h)
(j) infecting mammalian cells with the SBV harvested in step (i),
(k) cultivating the infected cells of step (j), and
(l) harvesting the SBV produced by said cells in step (k), and optionally
(m) infecting insect cells with the SBV harvested in step (l),
(n) cultivating the infected cells of step (m), and
(o) harvesting the SBV produced by said cells in step (n).

The insect cells used in the method for the production of SBV of the invention are preferably KC cells.

As mammalian cells preferably BHK cells, in particular BHK-21 cells, are used in the method for the production of SBV according to the invention.

Most preferably, in the method for the production of SBV according to the invention the insect cells are KC cells, and the mammalian cells are BHK cells, in particular BHK-21 cells.

Further, the invention also comprises the SBV obtainable by the method for the production of SBV according to the invention.

The invention further provides a method for the production of inactivated SBV or of an immunogenic composition of the invention comprising the steps of:
(A) infecting cells with a SBV, wherein the cells are in particular monkey kidney cells, preferably Ma104 cells or Ma104-AK cells, or wherein the cells are BHK cells, preferably BHK-21 cells,
(B) cultivating the infected cells,
(C) harvesting the SBV produced by said cells, and
(D) inactivating said SBV by heat treatment or with a virus inactivating agent If preferably Ma104 cells or Ma104-AK cells are used in the method for the production of inactivated SBV or of the immunogenic composition of the invention, this has the advantage that adverse reactions, in particular allergic reactions, can be reduced or minimized if the inactivated SBV or the immunogenic composition produced by said method is administered to an animal.

In particular, it is preferred if in step (A) of the method for the production of inactivated SBV or of the immunogenic composition of the invention the cells are infected with a SBV obtainable by the method for the production of SBV of the invention.

The invention thus also provides the combination of (i) the method of producing an infectious SBV of the invention and (ii) the method for the production of inactivated SBV or of the immunogenic composition of the invention, wherein said methods are performed subsequently.

Preferably, in the method for the production of infectious SBV of the invention and/or in the method for the production of inactivated SBV or of the immunogenic composition according to the invention, the cells are infected with SBV at an MOI of 0.00001-0.01, preferably at an MOI of 0.0001-0.001.

In particular it is preferred, if in the method for the production of SBV according to the invention and/or in the method for the production of inactivated SBV or of the immunogenic composition of the invention, the cells are cultivated in a medium containing 1-10% FCS, more preferably containing 2-6% FCS, and/or if the cells are cultivated at a temperature of 25-38° C., preferably of 36-38° C., more preferably of about 37° C. It is also possible to cultivate the cells in the absence of FCS.

Also, the invention comprises SBV obtainable by the method for the production of inactivated SBV or of the immunogenic composition of to the invention, and, moreover, the invention also provides inactivated SBV obtainable by the combination of (i) the method of producing an infectious SBV of the invention and (ii) the method for the production of inactivated SBV or of the immunogenic composition of the invention, wherein said methods are performed subsequently.

In another aspect, it is preferred if in the method for the production of infectious SBV of the invention and/or in the method for the production of inactivated SBV or of the immunogenic composition of the invention, the SBV comprises
a small (S) RNA segment having a sequence that is inverse complementary to a nucleic acid sequence having at least 97.8%, preferably at least 99% sequence identity with the nucleic acid sequence of SEQ ID NO:1 or SEQ ID NO:7,
a medium (M) RNA segment having a sequence that is inverse complementary to a nucleic acid sequence having at least 82.2% sequence identity with the nucleic acid sequence of SEQ ID NO:2, and/or
a large (L) RNA segment having a sequence that is inverse complementary to a nucleic acid sequence having at least 93% sequence identity with the nucleic acid sequence of SEQ ID NO:3,
and/or wherein said SBV comprises
an S RNA segment, characterized in that the S RNA segment has a sequence having at least 97.8%%, preferably at least 99% sequence identity to SEQ ID NO:4 or SEQ ID NO:8,
an M RNA segment, characterized in that the M RNA segment has a sequence having at least 82.2% sequence identity to SEQ ID NO:5, and/or
an L RNA segment, characterized in that the L RNA segment has a sequence having at least 93% sequence identity to SEQ ID NO:6.

The invention also provides a SBV, preferably an isolated SBV, comprising
a small (S) RNA segment having a sequence that is inverse complementary to a nucleic acid sequence having at least 97.8%, preferably at least 99% sequence identity with the nucleic acid sequence of SEQ ID NO:1 or SEQ ID NO:7, a medium (M) RNA segment having a sequence that is inverse complementary to a nucleic acid sequence having at least 82.2% sequence identity with the nucleic acid sequence of SEQ ID NO:2, and/or a large (L) RNA segment having a sequence that is inverse complementary to a nucleic acid sequence having at least 93% sequence identity with the nucleic acid sequence of SEQ ID NO:3.

The invention further provides a preferably isolated SBV, in particular the aforementioned SBV, which comprises an S RNA segment, characterized in that the S RNA segment has a sequence having at least 97.8% sequence identity to SEQ ID NO:4 or SEQ ID NO:8, an M RNA segment, characterized in that the M RNA segment has a sequence having at least 82.2% sequence identity to SEQ ID NO:5, and/or an L RNA segment, characterized in that the L RNA segment has a sequence having at least 93% sequence identity to SEQ ID NO:6.

Also the invention comprises a composition of matter obtainable by any of the aforementioned methods, wherein the composition is preferably an immunogenic composition, in particular a vaccine.

A further aspect of the invention relates to the use of the immunogenic composition of the invention for the preparation of a medicament for treating or preventing SBV and/or treating or preventing viremia or malformations induced by SBV and/or preventing or reducing the transmission of SBV in an animal in need of said treatment.

Also, the invention provides a method of generating an immune response to SBV in an animal comprising administering to said animal the immunogenic composition of the invention.

In another aspect, the invention provides a method of treating or preventing SBV or treating or preventing viremia or malformations induced by SBV in an animal in need of said treatment, comprising administering to said animal a therapeutically effective amount of the vaccine composition of the invention.

The invention further provides a method for inducing an immune response against SBV and/or preventing or reducing viremia or malformations induced by SBV and/or preventing or reducing the transmission of SBV in an animal or a herd of animals comprising the step of administering the immunogenic composition of the invention to an animal in need thereof.

In the aforementioned methods, the immunogenic composition of the invention or the vaccine of the invention, respectively, is preferably administered in a single dose or more preferably in two doses.

Example 1

Details about First SBV Isolation

BHK-21 cells have been extensively used for growth of Orthobyniaviruses. Following this, SBV virus was successfully isolated for the first time using this cell line, by FLI researchers in November 2011. Except for the BHK, *Culicoides variipennis* larvae cells (referred to as KC cells from Collection of Cell Lines in Veterinary Medicine, Friedrich-Loeffler-Institut, Greifswald-Insel Riems, Germany) were used. KC cells were incubated for 10 days with ultrasonically disrupted blood diluted in Schneider's media. The cells were then lysed by freezing and thawing. A monolayer of baby hamster kidney-21 cells (BHK, clone 13) was inoculated with the lysate. The inoculums was removed after 1 hour and replaced by Eagle minimal essential medium (EMEM). A strong cytopathic effect was visible after 5 days, and the culture supernatant tested positive for the novel virus, with a Cq value of approximately 14 in the specific cRT-qPCR (isolate 2) and $3\times10^6$ TCID50 per ml.

Manufacturing Process: General Description

The manufacturing process, as described below, is carried out following standard manufacturing methods, e.g. under conditions of sterility and after verification of correct operation conditions such as air filtration.

Description of Manufacturing Process:

1. Production of MSV (Master Stock Virus)

The SBV isolate 2 was used for MSV (Master Stock Virus) production. Roller bottle plated with BHK-21 cells ($5\times10^7$ cells) were infected at moi 0.0001. After 54 h of incubation roller bottle is frozen at −20, thawed and centrifugated at 2000 g for 5 min. Supernatant was collected and aliquots of 1 ml were stored at −80 C until further process.

2. Production of SBV Antigen

The BHK-21 cells (working cell stock—WCS) are stored frozen in liquid nitrogen. WCS was thawed and expanded on cell culture flasks (T160 $cm^2$) using EMEM media and 10% gamma irradiated FCS. Cells were trypsinised using recombinant (non animal origin) trypsin. One T160 flask was trypsinised and resuspended in 150 ml of EMEM media containing 2% FCS. This cell suspension was used to seed one roller bottle (495 $cm^2$). Roller bottles containing cell suspension were placed in 37 C incubator and roller at 0.5 rpm. Twelve to 16 h post plating cells were plated at density $5\times10^7$ per bottle. Infection using moi 0.0001 was used. Cells were continuously incubated at 37 C and rolled at 0.5 rpm for 50-56 h until specific SBV cytopathic effect (CPE) don't reach about 60-70% of cells. At this time point the complete roller bottle flasks were frozen at −20 C and thawed in 37 C water bath and stored at −80 C until further process.

The virus titration is performed following procedure:

Materials Needed

1. BHK-21 cells (clone 13)
2. T75 flasks
3. Flat bottom 96 wells plates
4. Flat bottom 48 wells plates
5. Thermo 8-channel matrix pipette+tips
6. Eppendorf 8-channel pipette 50-1250+tips
7. Reservoir for multichannel pipettes
8. Trypisn+edta
9. Media ZB5
10. Pipettes 5, 10 and 25 ml
11. Pipetboy
12. Inverted microscope Procedure Highly confluent T75 flask trypsinize and cells nicely resuspend in 20 ml of media (10% FCS).

Add 100 ml of media (0% FCS) and mix well

This cell suspension pours into reservoir for multichannel pipettes

Use multichannel pipette to fill 100 µl of cell suspension into the wells of first 8 columns of 96 wells plates Leave plates at 37° C. in CO2 incubator for 6-12 h to attach After this time prepare 48 wells plate and fill 1080 µl of serum free media in each well In the wells of the first column inoculate 120 µl of material for titration Using eppendorf 8-channel pipette with the program P/M (pipette 120 µl and mix 620 µl four times) firstly mix the first column where the material is inoculated Discard tips
From the wells of the first column (with the new tips) pipette 120 µl into second and mix
Discard tips
Repeat this process until you finish the last column
Using matrix pipette aspirate 800 µl from the first row of 48 well plate (which contains serial dilutions of one sample)
When attaching tips press firmly, but not too strong as the matrix function will not work
Dispense 100 µl in 8 rows of 96 wells plate
Incubate at 37 C for period of 3-4 days
Read results on inverted microscope 3. Vaccine Formulations 3.1 Inactivation Procedure The process of inactivation of the final antigen lasts for a total of 72 hours, and the concentration of BEI used is 15 mM. Final antigen is inactivated by adding BEI 0.1 M at a proportion of 100 ml per liter of antigen being inactivated (final concentration 10 mM). After the addition of the BEI the mixture is homogenized for at least 15 minutes and the pH is verified. After the homogenization process, the mixture is decanted into a sterile container where it is kept in agitation, at 37+/−1° C., for 24 hours. After 24 hours, a second inactivation of the final antigen is carried out by means of adding BEI 0.1 M at a proportion of 50 ml per liter of antigen being inactivated (final concentration 5 mM). After the second addition of BEI, the process is repeated under the same conditions as described above for the first addition, but maintaining the mixture in agitation for 48 hours.

3.2 Neutralization of Residual BEI

Once the inactivation process has been completed, 1 M sodium thiosulphate solution is added at the proportion of 5 ml per liter of inactivated antigen (final concentration 5 mM), in order to neutralize the BEI. After the mixture has been homogenized, the pH is verified. If necessary, an adjustment is done with hydrochloric acid, to obtain a pH of 7.2+−0.2.

3.3 Adjuvants

Alhydrogel (aluminium hydroxide) and Quil-A (saponin) are used as adjuvants.

4. Proof of Concept Experiment in Cattle.

Eighteen (18)-7 month old cattle are used for the experiment. Animals are been divided into four groups with four animals in each group, while other two animals are used as contact controls. All animals are SBV sero-negative at the beginning of experiment. First group (of four animals) is vaccinated with the vaccine dose containing $10^6$ SBV TCID50/ml, the second with $10^5$ SBV TCID50/ml, third with $10^4$ SBV TCID50/ml and finally fourth group is not vaccinated as well as two animals within contact control. Within each group 4 animals are vaccinated by the subcutaneous route (2 mL) and revaccinated 3 weeks later. All animals in the study are challenged two weeks after re-vaccination (challenge dose=$10^7$ TCID50 of live virus/animal) except of contact control animals. All non vaccinated animals develop viremia upon SBV challenge, staring at 3 dpi (days post infection) and lasting 2-3 days. Animals vaccinated show significantly lower viremia and reduced to no clinical symptoms compared to non-vaccinated animals after the SBV challenge.

Example 2

1. Introduction

In this study, several inactivated vaccine formulations have been produced and subsequently tested in sheep and cattle regarding their ability to induce neutralising antibodies and to prevent viraemia after experimental challenge infection.

2. Materials and Methods

Vaccines

Five different prototype vaccine formulations were produced (Table 1); all of them were inactivated SBV preparations in aqueous solution. SBV was either grown on two different baby hamster kidney (BHK-21) cell lines (vaccines "BHKCT-HT", "BHK13-HT", "BHK13-LT") or on MA-104 cells (vaccines "MA-HT" and "MA-LT").

The antigen-concentration was formulated using the infectious titre of SBV before inactivation with binary ethylenimine (BEI) using either a long (using 10 mM of BEI for 72 hours at 37° C.) or a short (using 2 mM of BEI for 12 hours at 37° C.) protocol.

Vaccine candidates contained antigen concentration as follows: 6.1 log 10 50% tissue culture infectious doses per ml ($TCID_{50}$/ml) (MA-HT) or 5.7 log 10 $TCID_{50}$/ml (BHKCT-HT, BHK13-HT, MA-LT) or 4.7 log 10 $TCID_{50}$/ml (BHK13-LT). Saponin and aluminium hydroxide were used as adjuvants (0.125 µg Saponin per 1 ml and 6.65 mg aluminium hydroxide per ml in all vaccine candidate formulations). All formulations were tested for the absence of bacterial contamination and in duplicates for successful inactivation by two subsequent passages in BHK-21 cells. The pH values of each prototype vaccine were adjusted at 6.8-7.2 at 20° C. The vaccines were kept at 4° C. until use.

TABLE 1

Vaccines and animal groups.

| Vaccines Name | Cell line | Infectious titre used | Inactivation | Animals Animal group | Animal number |
|---|---|---|---|---|---|
| BHKCT-HT | BHK-21 clone CT | 5.7 log10 $TCID_{50}$/ml | long protocol | A (sheep) | S01-S05 |
|  |  |  |  | G (cattle) | C01-C06 |
| BHK13-HT | BHK-21 clone 13 | 5.7 log10 $TCID_{50}$/ml | short protocol | B (sheep) | S06-S10 |
| BHK13-HT | BHK-21 clone 13 | 4.7 log10 $TCID_{50}$/ml | short protocol | C (sheep) | S11-S15 |
| MA-HT | MA-104 | 6.1 log10 $TCID_{50}$/ml | short protocol | D (sheep) | S16-S20 |
|  |  |  |  | H (cattle) | C07-C10 |
| MA-HT | MA-104 | 5.7 log10 $TCID_{50}$/ml | long protocol | E (sheep) | S21-S25 |
|  |  |  |  | I (cattle) | C11-C16 |
| unvaccinated control |  |  |  | F (sheep) | S26-S30 |
|  |  |  |  | K (cattle) | C17-C22 |

Animals

Twenty-five SBV-naive sheep of European domestic breeds (7-9 months of age) were assigned to 5 groups of 5 animals each, which were immunised subcutaneously with one of the prototype vaccines (see table 1). Another 5 sheep were kept as unvaccinated controls. Male and female animals were distributed equally.

In addition, 22 SBV antibody-negative female Holstein-Friesian cattle were assigned to four groups of four (group H) or six animals (groups G, I and K) each. Animals in group G, H and I were immunised subcutaneously with vaccines BHKCT-HT, MA-HT and MA-LT, respectively. Cattle in group K were kept as unvaccinated controls. On the day of the first vaccination, the animals were between 8 and 12 months of age.

In each case, the animals were vaccinated twice three weeks apart and three weeks after the second vaccination both vaccinated and control animals were inoculated with 2×0.5 ml of an SBV field strain that was only passaged in the natural host. During the entire study, rectal body temperatures were measured daily, and the animals were examined for clinical signs by veterinarians.

Sampling, Real-Time RT-PCR and Serology

Following the first vaccination, serum samples were collected at days 0, 3, 4, 7 and weekly thereafter. After the second vaccination, serum samples were taken in weekly intervals. Following challenge infection, serum samples were taken daily during the first eight days and on days 14 and 21. Samples of spleen, tonsils, and mesenteric and mandibular lymph nodes were taken at autopsy on days 22-29 after challenge infection and homogenized in 1 ml MEM.

RNA from serum and tissue samples taken at autopsy was extracted using the MagAttract Virus Mini M48 Kit for automated extraction (Qiagen, Germany) according to the manufacturer's recommendations. SBV genome loads were determined by a reverse transcription real-time PCR (RT-qPCR) (7) with an external standard based on the S genome segment. Furthermore, serum samples were analyzed with a commercially available SBV antibody ELISA (ID Screen® Schmallenberg virus Indirect, IDvet, France) using the recommended cut-off of 70% relative optical density compared to the positive control, and in a standard micro-neutralisation assay.

3. Results

Clinical Observations and Post-Mortem Examinations

Following the first vaccination with the vaccine prototypes no adverse side effects were observed; none of the animals showed fever or any other clinical sign. After the second vaccination one cattle immunised with vaccine MA-HT (group H) developed a low-grade swelling at the injection site for 2 days.

After the challenge infection, one unvaccinated cattle developed fever on day 3, another showed mild diarrhea for three days. One animal out of group I had nasal discharge for one day.

Autopsy of the animals did not reveal any significant gross lesions. The mesenteric lymph nodes of all but one (S30) unvaccinated animals were PCR-positive; on average 2.86E+03 genome copies per mg (copies/mg) were detected. In addition, SBV RNA was found in the mandibular lymph nodes of 3 out of 5 unvaccinated sheep (S27-S29) and of all control cattle (average 2.68E+01 copies/mg), the tonsils of S27-S29 and C18-C20 (average 9.90E+01 copies/mg), and spleens of 4 out of 5 unvaccinated sheep (S26-S29; average 4.57E+03 copies/mg) and of two control calves (C17, C21; average 1.40E+01 copies/mg). No viral RNA was detected in any of the vaccinated animals.

Antibody Response

On the day of the first vaccination, all animals were negative in both serological assays.

Before challenge infection, no antibodies could be detected in the unvaccinated animals. Three weeks after infection all but one (S30) control sheep and cattle scored positive in the neutralisation assay. Antibodies were found in cattle and in 2 out of the 5 unvaccinated sheep (S26, S29) by ELISA as well. Despite an increasing sample OD relative to the positive control OD value (S/P) both the control sheep S27 and S28 scored negative in the ELISA.

Three weeks after the first immunisation with vaccine BHKCT-HT, BHK13-HT or BHK13-LT (SBV grown on BHK cells), all sheep and cattle were negative in the ELISA, while in S07, S08, S10 (BHKCT-HT), and S04 (BHK13-HT) low antibody titres were detected in the neutralisation assay. Following the second vaccination antibodies were detected in at least one serological assay, in most cases a considerable increase of neutralising antibodies was seen. Three weeks after challenge infection 8 out of 15 sheep (S04, S06, S07, S09, S10, S11, S12, S15) and 5 out of 6 cattle (C01-C05) were positive in both assays, 7 sheep (S01-S03, S05, S08, S13, S14) and the remaining cattle (C6) were positive in the neutralisation test only, and S15 in the ELISA assay only.

After one immunisation with vaccines MA-HT or MA-LT (SBV grown on MA-104 cells), all cattle and all but two sheep scored negative in both serological assays. S22 and S23 had titres of 1:5 and 1:7, respectively, in the neutralisation assay. Following the second vaccination, in S19, S24, C08, and C14 no antibodies could be detected. S16, S21, C07, C09, and C10 scored positive in both serological assays, while the remaining animals were positive in the neutralisation assay only. Three weeks after challenge infection all sheep of group D and 4 out of 5 sheep of group E were positive in the neutralisation assay, in animal S16 antibodies could be detected by the ELISA, and animal S24 was negative in both assays. In all cattle of group H (high titre of SBV) antibodies were detectable by ELISA and neutralisation assay. The same is true for C12 and C13 (group I, low SBV titre), C11, C15, and C16 scored positive only in the neutralisation assay, and in C14 no antibodies could be detected by any test.

After the second immunisation an increase of the average neutralising antibody titers were observed, while after challenge infection, most of the neutralisation titers remained constant in all vaccinated groups.

Real-Time RT-PCR

Following the first vaccination SBV genome was not detected in any animal (data not shown), confirming the successful inactivation of SBV with short and long BEI inactivation procedure.

After challenge infection, all but one (S30) unvaccinated sheep scored positive in the RT-qPCR between day 2 and 4 (S27-S29) or 5 (S26). In 1 out of 6 unvaccinated cattle (C19) SBV-genome was first detectable on day 1 after infection, the other 5 calves scored positive on day 2 for the first time. SBV genome remained detectable until day 5 (C17, C19-C21), 6 (C22) or 7 (C18). Three out of 6 cattle immunised with vaccine MA-LT (C12, C13, C16) were positive in the RT-qPCR on day 3, while the animals vaccinated with MA-HT vaccines did not develop RNAemia (RNA in the blood) upon challenge.

In serum samples taken from all vaccinated sheep, from control sheep S30, and from all cattle of groups G and H (high titer vaccine groups), viral RNA could not be detected following challenge infection.

4. Conclusion

Five different inactivated vaccine formulations have been developed and were subsequently tested in cattle and sheep. In the experiments none of the animals showed significant adverse effects and all of the animals seroconverted upon vaccination. Furthermore, majority but not all the animals developed detectable neutralizing SBV antibodies levels upon vaccination. Importantly, upon challenge infection, RNAemia was completely prevented by four prototype vaccines and considerably reduced by the fifth. Those data suggest that protection from virus infection is only partially mediated by neutralizing antibodies and that additional still undetermined mechanisms, most likely associated with cellular immunity, essentially contributed to virus clearance upon SBV challenge. The two major characteristics of inactivated vaccines are (i.) the complete inactivation of the infectious virus, which was demonstrated by cell culture passages and the missing RNAemia after the first immunisation, and (ii.) the induction of protective immunity. Although neutralising antibodies were not detected in every vaccinated animal prior to challenge infection, RNAemia was completely prevented by four prototype vaccines and considerably reduced by the fifth. The detection of viral RNA in the lymphoreticular system was used as diagnostic tool apart from RNAemia in the present study. In contrast to the controls all vaccinated animals were clearly negative for SBV-RNA in the lymphoid system (in the lymphoid organs at the time of autopsy) like the mesenteric lymph nodes. One of the unvaccinated control sheep showed neither RNAemia, nor RT-qPCR-positive tissue samples, nor seroconversion after challenge infection, the reason for that observation remains unclear. Possible explanations are a failed injection or a status of (natural) resistance to SBV infection.

Nevertheless, the absence of detectable RNA in most vaccine groups allows to draw the conclusion that, if even no viral genomes can be detected (in the serum), no challenge virus could be transmitted to the foetus.

Although RNAemia was prevented or markedly reduced by vaccination, antibodies were not detected in every animal prior to challenge infection in every test. Overall, the correlation of ELISA test and neutralisation assay was greater in bovine than in ovine samples, especially after challenge infection of unvaccinated animal.

The highest levels of antibodies of all sheep groups were detected by neutralisation test after challenge infection of unvaccinated sheep. The same was observed after immunisation with several Rift Valley fever vaccines and subsequent challenge (8), where the applied vaccines, however, did not provide sterile immunity, but only a reduction of viraemia. As opposed to this, the SBV vaccine prototypes characterized in this study prevented RNAemia in sheep completely despite a low level of neutralising antibodies.

In our study, the titre of neutralising antibodies was influenced by the production cell line and the viral titre prior to inactivation. A dose dependence of the cell culture supernatant used for vaccine preparation was described for AKAV as well, independent whether inactivated or attenuated live vaccines were used (9; 10). At least $10^{5.5}$ TCID$_{50}$/ml of virus were reported to be necessary for vaccine development. As 2 ml of a vaccine containing 6.1 log 10 TCID$_{50}$/ml virus grown on MA-104 cells prevented RNAemia completely, but in half of the calves which were immunized with 5.7 log 10 TCID$_{50}$/ml viral genome was detectable for one day, a similar minimal dose may be assumed for SBV. However, in vaccines produced on BHK-21-cells, the lower viral titre (5.7 log 10 TCID50/ml) prevented RNAemia completely in both animal species, in sheep merely 4.7 log 10 TCID50/ml were necessary.

In conclusion, in this proof-of-concept characterization of different vaccine candidates, a high efficacy could be demonstrated for four out of five SBV vaccine prototypes in both major target species. As a result, the development of a killed vaccine against Schmallenberg virus, which is efficacious and safe in cattle and sheep, is demonstrated. The results obtained in this study show that inactivated SBV vaccine can be successfully applied to support efforts for SBV spread control as well as disease prevention in domestic ruminants.

Example 3

In the following, an alternative inactivation procedure and subsequent neutralization process is described, which also allowed the production (the further steps of production were performed in accordance with Example 1) of an effective vaccine for a successful prevention of infection with SBV:

Inactivation Procedure

The process of inactivation of the final antigen lasted for a total of 12 hours, and the concentration of BEI used was 2 mM. Final antigen was inactivated by adding BEI 0.17 M at a proportion of 11.9 ml per liter of antigen being inactivated (final concentration 2 mM). After the addition of the BEI, the mixture was kept in agitation, at $37+/-1°$ C., for 12 hours.

Neutralization of Residual BEI

Once the inactivation process has been completed, 1 M sodium thiosulphate solution was added at the proportion of 10 ml per liter of inactivated antigen (final concentration 10 mM), in order to neutralize the BEI.

Example 4

Hereinafter, an alternative production of MSV (master stock virus) is described, which likewise enabled the manufacturing (the further steps of the manufacture process were performed in accordance with Example 1, wherein the inactivation procedure was done as described in Example 3) of an effective vaccine for a successful prevention of infection with SBV:

5. Production of MSV (Master Stock Virus)

The SBV isolate 2 was used for MSV (Master Stock Virus) production. Roller bottle plated with Ma104-Ak ($5\times10^7$ cells) were infected at moi 0.0001. After 54 h of incubation roller bottle is frozen at −20, thawed and centrifugated at 2000 g for 5 min. Supernatant was collected and aliquots of 1 ml were stored at −80 C until further process.

6. Production of SBV Antigen

The Ma104-Ak (working cell stock—WCS) are stored frozen in liquid nitrogen. WCS was thawed and expanded on cell culture flasks (T160 cm$^2$) using EMEM media and 10% gamma irradiated FCS. Cells were trypsinised using recombinant (non animal origin) trypsin. One T160 flask was trypsinized and resuspended in 150 ml of EMEM media containing 2% FCS. This cell suspension was used to seed one roller bottle (495 cm$^2$). Roller bottles containing cell suspension were placed in 37 C incubator and roller at 0.5 rpm. Twelve to 16 h post plating cells were plated at density $5\times10^7$ per bottle. Infection using moi 0.001 was used. Infected cells were continuously incubated at 37 C and rolled at 0.5 rpm for 72-96 h until specific SBV cytopathic effect (CPE) don't reach about 60-70% of cells. At this time point the complete roller bottle flasks were frozen at −20 C and thawed in 37 C water bath and stored at −80 C until further process.

In the Sequence Listing

SEQ ID NO:1 corresponds to the complete genomic sequence of a S segment of an infectious Schmallenberg virus (BH80/11-4),
SEQ ID NO:2 corresponds to the complete genomic sequence of a M segment of an infectious Schmallenberg virus (BH80/11-4),
SEQ ID NO:3 corresponds to the complete genomic sequence of a L segment of an infectious Schmallenberg virus (BH80/11-4),
SEQ ID NO:4 corresponds to anti-parallel (i.e. complementary and inverse) RNA sequence of SEQ ID NO:1,
SEQ ID NO:5 corresponds to the anti-parallel RNA sequence of SEQ ID NO:2,
SEQ ID NO:6 corresponds to the anti-parallel RNA sequence of SEQ ID NO:3,
SEQ ID NO: 7 corresponds to SEQ ID NO:1, wherein the nucleotide at position 9 is "a" instead of "g", and
SEQ ID NO: 8 corresponds to the anti-parallel RNA sequence of SEQ ID NO:7 and thus corresponds to SEQ ID NO:4, wherein the nucleotide at position 831 is "u" instead of "c".

REFERENCES

All references cited herein are hereby entirely incorporated by reference.
1. B. Hoffmann, M. Scheuch, D. Höper, R. Jungblut, M. Holsteg, H. Schirrmeier, M. Eschbaumer, K. V. Goller, K. Wernike, M. Fischer, A. Breithaupt, T, C. Mettenleiter, M. Beer, Novel orthobunyavirus in Cattle, Europe, 2011. *Emerg. Infect. Dis.* 18, 469-472 (2012).
2. M.-M. Gariglinany et al., Schmallenberg virus in calf born at term with porencephaly, Belgium. *Emerg. Infect. Dis.* 18 (2012), doi: 10.3201/eid1806.120104.
3. M. D. Bowen et al., A reassortant bunyavirus isolated from acute hemorrhagic fever cases in Kenya and Somalia. *Virology.* 291, 185-190 (2001).
4. A. M. Q. King, M. J. Adams, E. B. Carstens, E. J. Lefkowitz, Eds., *Virus Taxonomy: Ninth Report of the International Committee on Taxonomy of Viruses.* (Elsevier, San Diego, USA, 2011), pp 725-731.
5. R. M. Kinney, C. H. Calisher, Antigenic relationships among Simbu serogroup (Bunyaviridae) viruses. *Am. J. Trop. Med. Hyg.* 30, 1307-1318 (1981).
6. M. F. Saeed, L. Li, H. Wang, S. C. Weaver, A. D. Barrett, Phylogeny of the Simbu serogroup of the genus Bunyavirus. *J. Gen. Virol.* 82, 2173-2181 (2001).
7. Bilk S, Schulze C, Fischer M, Beer M, Hlinak A, Hoffmann B. Organ distribution of Schmallenberg virus RNA in malformed newborns. Veterinary microbiology 2012 Mar. 30.
8. Kortekaas J, Antonis A F, Kant J, Vloet R P, Vogel A, Oreshkova N, et al. Efficacy of three candidate Rift Valley fever vaccines in sheep. Vaccine 2012 May 14; 30(23): 3423-9.
9. Kurogi H, Inaba Y, Takahashi E, Sato K, Goto Y, Satoda K, et al. Development of inactivated vaccine for Akabane disease. National Institute of Animal Health quarterly 1978 Winter; 18(3-4):97-108.
10. Kurogi H, Inaba Y, Akashi H, Takahashi E, Sato K, Satoda K, et al. Immune response of various animals to Akabane disease live virus vaccine. National Institute of Animal Health quarterly 1979 Summer; 19(1-2):23-31.

What is claimed is:

1. An immunogenic composition comprising saponin, aluminum hydroxide, and an aziridine compound-inactivated Schmallenberg virus (SBV), wherein the inactivated SBV comprises a medium (M) RNA segment having a sequence that is inverse complementary to a nucleic acid sequence having at least 95% sequence identity with the nucleic acid sequence of SEQ ID NO:2 over the whole length of SEQ ID NO:2.

2. The immunogenic composition according to claim 1, wherein the inactivated SBV further comprises:
   (a) a small (S) RNA segment having a sequence that is inverse complementary to the nucleic acid sequence of SEQ ID NO:7 over the whole length of SEQ ID NO:7;
   (b) a medium (M) RNA segment that is inverse complementary to a nucleic acid sequence of SEQ ID NO:2 over the whole length of SEQ ID NO:2; and
   (c) a large (L) RNA segment that is inverse complementary to a nucleic acid sequence of SEQ ID NO:3 over the whole length of SEQ ID NO:3.

3. The immunogenic composition according to claim 1, wherein the aziridine compound is binary ethyleneimine (BEI).

4. The immunogenic composition according to claim 1, comprising an amount of SBV which is equivalent to a virus titer of at least about $10^5$ $TCID_{50}$/mL per dose.

5. The immunogenic composition according to claim 1, wherein the SBV has a pre-inactivation titer of at least about $10^6$ SBV particles per milliliter.

6. The immunogenic composition according to claim 1, further containing one or more pharmaceutically acceptable carriers or excipients.

7. The immunogenic composition according to claim 6, wherein said one or more pharmaceutically acceptable carriers or excipients are selected from the group consisting of solvents, dispersion media, adjuvants, stabilizing agents, diluents, preservatives, antibacterial and antifungal agents, isotonic agents, and adsorption delaying agents.

8. A vaccine composition for the treatment of Schmallenberg associated disease in an animal selected from the group consisting kyphosis, lordosis, scoliosis, and torticollis of the vertebral column macrocephaly and brachygnathia inferior of the scull; and hydracephaly, porencephaly, cerebellar hypoplasia, and hypoplasia of the brain stem comprising administration of a therapeutic dose to the animal in need thereof of the immunogenic composition according to claim 1.

9. A vaccine composition for the reduction of the viremia or malformations induced by SBV comprising the immunogenic composition according to claim 1.

10. A vaccine composition for the reduction of the transmission of SBV, which comprises the immunogenic composition according to claim 1.

11. A method for the production of the immunogenic composition according to claim 1, comprising the steps of
   (A) infecting cells with a SBV that comprises a medium (M) RNA segment having a sequence that is inverse complementary to a nucleic acid sequence having at least 95% sequence identity with the nucleic acid sequence of SEQ ID NO: 2 over the whole length of SEQ ID NO: 2;
   (B) cultivating the infected cells;
   (C) harvesting the SBV produced by said cells; and
   (D) inactivating said viral particles an aziridine compound.

12. The method according to claim 11, wherein the cells are monkey kidney cells or BHK cells.

13. The method according to claim 12, wherein the monkey kidney cells are Ma104 cells or Ma104-AK cells, and the BHK cells are BHK-21 cells.

14. The method according to claim 11, wherein the cells are infected with SBV at an MOI of 0.00001-0.01.

15. The method according to claim 11, wherein the cells are infected with SBV at an MOI of 0.0001-0.001.

16. The method according to claim 11, wherein the cells are cultivated in a medium comprising about 0% FCS.

17. The method according to claim 11, wherein the cells are cultivated in a medium comprising about 1-10% FCS.

18. The method according to claim 11, wherein the cells are cultivated in a medium comprising about 2-6% FCS.

19. The method according to claim 11, wherein the cells are cultivated at a temperature of 25-38° C.

* * * * *